(12) United States Patent
Jones et al.

(10) Patent No.: US 8,617,198 B2
(45) Date of Patent: *Dec. 31, 2013

(54) TISSUE EXPANDERS AND METHODS OF USE

(75) Inventors: Christopher S. Jones, Menlo Park, CA (US); Daniel Jacobs, Palo Alto, CA (US); F. Mark Payne, Palo Alto, CA (US); David S. Mintz, Mountain View, CA (US); Craig A. Purdy, Campbell, CA (US); Ryan S. Han, Saratoga, CA (US); Tadmor Shalon, Palo Alto, CA (US)

(73) Assignees: AirXpanders, Inc., Palo Alto, CA (US); Shalon Ventures, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/313,919

(22) Filed: Dec. 7, 2011

(65) Prior Publication Data

US 2012/0078366 A1  Mar. 29, 2012

Related U.S. Application Data

(63) Continuation of application No. 12/973,693, filed on Dec. 20, 2010, which is a continuation-in-part of application No. 11/231,482, filed on Sep. 21, 2005.

(60) Provisional application No. 60/612,018, filed on Sep. 21, 2004, provisional application No. 60/688,964, filed on Jun. 9, 2005, provisional application No. 61/288,197, filed on Dec. 18, 2009.

(51) Int. Cl.
*A61M 29/00* (2006.01)
*A61F 2/12* (2006.01)

(52) U.S. Cl.
USPC .............................. 606/192; 623/8

(58) Field of Classification Search
USPC .................... 623/7–8; 606/198, 192
See application file for complete search history.

(56) References Cited

U.S. PATENT DOCUMENTS

| | | | |
|---|---|---|---|
| 3,174,455 A | | 3/1965 | Peterson |
| 3,600,718 A | * | 8/1971 | Boone ............................. 623/8 |
| 3,852,833 A | * | 12/1974 | Koneke et al. ................... 623/7 |
| 3,934,274 A | | 1/1976 | Hartley, Jr. |
| 4,217,889 A | | 8/1980 | Radovan et al. |
| 4,264,990 A | | 5/1981 | Hamas |
| 4,550,720 A | * | 11/1985 | Trick .............................. 600/40 |
| 4,574,780 A | | 3/1986 | Manders |
| 4,615,704 A | | 10/1986 | Frisch |

(Continued)

FOREIGN PATENT DOCUMENTS

| | | |
|---|---|---|
| EP | 0197726 B1 | 1/1992 |
| EP | 0469165 A1 | 2/1992 |

(Continued)

OTHER PUBLICATIONS

Adler et al.; Tissue Expander Infections in Pediatric Patients; Plast Reconstr Surg; vol. 125; No. 2; pp. 484-489; Aug. 2009.

(Continued)

*Primary Examiner* — Suzette J Gherbi
(74) *Attorney, Agent, or Firm* — Shay Glenn LLP

(57) ABSTRACT

Tissue expanders and their methods of use.

12 Claims, 26 Drawing Sheets

(56) References Cited

U.S. PATENT DOCUMENTS

| | | | |
|---|---|---|---|
| 4,643,733 | A | 2/1987 | Becker |
| 4,651,717 | A | 3/1987 | Jakubczak |
| 4,666,447 | A | 5/1987 | Smith et al. |
| 4,671,255 | A | 6/1987 | Dubrul et al. |
| 4,773,908 | A | 9/1988 | Becker |
| 4,841,992 | A | 6/1989 | Sasaki et al. |
| 4,899,764 | A * | 2/1990 | Gauger .......... 128/899 |
| 4,950,292 | A | 8/1990 | Audretsch |
| 4,952,419 | A | 8/1990 | De Leon et al. |
| 4,955,905 | A | 9/1990 | Reed |
| 4,969,899 | A * | 11/1990 | Cox, Jr. .......... 623/8 |
| 5,005,591 | A | 4/1991 | Austad |
| 5,049,106 | A | 9/1991 | Kim et al. |
| 5,092,348 | A | 3/1992 | Dubrul et al. |
| 5,109,875 | A | 5/1992 | Gottlieb |
| 5,129,915 | A | 7/1992 | Cantenys |
| 5,133,753 | A | 7/1992 | Bark et al. |
| 5,141,508 | A | 8/1992 | Bark et al. |
| 5,146,933 | A * | 9/1992 | Boyd .......... 128/899 |
| 5,236,454 | A | 8/1993 | Miller |
| 5,318,533 | A | 6/1994 | Adams et al. |
| 5,376,117 | A | 12/1994 | Pinchuk et al. |
| 5,383,929 | A * | 1/1995 | Ledergerber .......... 623/8 |
| 5,480,430 | A | 1/1996 | Carlisle et al. |
| 5,496,368 | A | 3/1996 | Wiese |
| 5,525,275 | A | 6/1996 | Iversen et al. |
| 5,571,178 | A * | 11/1996 | Ledergerber .......... 623/8 |
| 5,571,179 | A | 11/1996 | Manders et al. |
| 5,653,726 | A | 8/1997 | Kieturakis |
| 5,658,330 | A | 8/1997 | Carlisle et al. |
| 5,720,762 | A | 2/1998 | Bass |
| 5,728,064 | A | 3/1998 | Burns et al. |
| 5,776,159 | A | 7/1998 | Young |
| 5,817,325 | A | 10/1998 | Sawan et al. |
| 5,849,311 | A | 12/1998 | Sawan et al. |
| 5,855,588 | A | 1/1999 | Young |
| 5,869,073 | A | 2/1999 | Sawan et al. |
| 5,938,669 | A | 8/1999 | Klaiber et al. |
| 5,964,803 | A | 10/1999 | Iversen et al. |
| 6,030,632 | A | 2/2000 | Sawan et al. |
| 6,055,989 | A | 5/2000 | Rehnke |
| 6,071,309 | A | 6/2000 | Knowlton |
| 6,126,931 | A | 10/2000 | Sawan et al. |
| 6,180,584 | B1 | 1/2001 | Sawan et al. |
| 6,187,043 | B1 * | 2/2001 | Ledergerber .......... 623/8 |
| 6,203,570 | B1 | 3/2001 | Baeke |
| 6,264,936 | B1 | 7/2001 | Sawan et al. |
| 6,494,879 | B2 | 12/2002 | Lennox et al. |
| 6,579,301 | B1 * | 6/2003 | Bales et al. .......... 606/191 |
| 6,645,225 | B1 | 11/2003 | Atkinson |
| 6,668,836 | B1 | 12/2003 | Greenburg et al. |
| 6,755,861 | B2 | 6/2004 | Nakao |
| 6,953,429 | B2 | 10/2005 | Forsell |
| 7,033,373 | B2 | 4/2006 | de la Torre et al. |
| 7,144,407 | B1 | 12/2006 | Lasersohn |
| 7,762,982 | B1 * | 7/2010 | Shah .......... 604/96.01 |
| 8,066,780 | B2 * | 11/2011 | Chen et al. .......... 623/23.65 |
| 8,394,118 | B2 * | 3/2013 | Jones et al. .......... 606/192 |
| 2001/0004709 | A1 * | 6/2001 | Dubrul .......... 623/8 |
| 2003/0074084 | A1 | 4/2003 | Nakao .......... 623/23.67 |
| 2004/0147953 | A1 * | 7/2004 | Gedebou .......... 606/198 |
| 2005/0116798 | A1 | 6/2005 | Bintoro et al. |
| 2005/0267595 | A1 | 12/2005 | Chen et al. |
| 2006/0069403 | A1 * | 3/2006 | Shalon et al. .......... 606/192 |
| 2006/0079727 | A1 | 4/2006 | Chernomorsky et al. |
| 2006/0111777 | A1 * | 5/2006 | Chen .......... 623/8 |
| 2006/0155261 | A1 | 7/2006 | Bek et al. |
| 2006/0235482 | A1 * | 10/2006 | Forsell .......... 607/39 |
| 2007/0032819 | A1 | 2/2007 | McEwen et al. |
| 2007/0197963 | A1 | 8/2007 | Griffiths et al. |
| 2007/0233273 | A1 | 10/2007 | Connell |
| 2008/0221704 | A1 | 9/2008 | Aray |
| 2009/0210056 | A1 * | 8/2009 | Forsell .......... 623/8 |
| 2010/0010531 | A1 * | 1/2010 | Shalon et al. .......... 606/192 |
| 2011/0152913 | A1 | 6/2011 | Jones et al. |

FOREIGN PATENT DOCUMENTS

| | | |
|---|---|---|
| EP | 0338701 B1 | 6/1992 |
| FR | 2615397 | 11/1988 |
| JP | 61-234852 | 10/1986 |
| JP | 8-173542 | 7/1996 |
| WO | WO 80/00302 A1 | 3/1980 |
| WO | WO 95/03752 A1 | 2/1995 |
| WO | WO 97/27829 A1 | 8/1997 |
| WO | WO 98/50100 A1 | 11/1998 |
| WO | WO 00/19914 A1 | 4/2000 |
| WO | WO 01/19283 A2 | 3/2001 |
| WO | WO 01/47441 A2 | 7/2001 |
| WO | WO 03/001966 A2 | 1/2003 |
| WO | WO 2004/043303 A2 | 5/2004 |
| WO | WO 2004/066812 A2 | 8/2004 |

OTHER PUBLICATIONS

Antony et al.; Acellular human dermis implantation in 153 immediate two-stage tissue expander breast reconstructions . . . ; Plast Reconstr Surg; vol. 125; No. 6; pp. 1606-1614; Jun. 2010.

Antony et al.; Salvage of tissue expander in the setting of mastectomy flap necrosis . . . ; Plast Recontr Surg; vol. 124; No. 2; pp. 356-363; Aug. 2009.

Argenta; Reconstruction of the Breast by Tissue Expansion; Clinic Plastic Surg; vol. 11; No. 2; pp. 257-264; Apr. 1984.

Armstrong et al.; Infection Following Breast Reconstruction; Ann Plast Surg; vol. 23; No. 4; pp. 284-288; Oct. 1989.

Austad; Evolution of the Concept of Tissue Expansion; Facial Plastic Surg; vol. 5; No. 4; pp. 277-279; Jul. 1988.

Beasley; Discussion: Eighty-four consecutive breast reconstructions using a textured silicone tissue expander (Maxwell); Plast Reconstr Surg; vol. 89; pp. 1035-1036; Jun. 1992.

Becker et al.; AlloDerm v DermaMatrix in immediate expander-based breast reconstruction . . . ; Plast Reconstr Surg; vol. 123; No. 1; pp. 1-6; Jan. 2009.

Bennett et al.; The History of Tissue Expansion; J Dermatol Surg Oncol; vol. 19; pp. 1066-1073; 1993.

Berge et al.; Tissue Expansion Using Osmotically Active Hydrogel Systems; Plast Reconstr Surg; vol. 108; No. 1; pp. 1-5; Jul. 2001.

Borba et al.; Self-inflating system of tissue expansion using gas (experimental study); Rev. Soc. Bras. Cir. Plast. Esthet. Reconstr.; vol. 9; pp. 70-78; 1993.

Brandi et al.; Carbon Dioxide Therapy: effects on skin irregularity and its use as a complement to liposuction; Aesth. Plast. Surg.; vol. 28; pp. 222R225; 2004.

Buck et al.; Accellular dermis-assisted breast reconstruction with the use of crescentric tissue expansion . . . ; Aesthet Surg J; vol. 30; No. 2; pp. 194-200; 2010.

Camilleri et al.; A review of 120 Becker permanent tissue expanders in reconstruction of the breast; Br J Plastic Surg; vol. 49; pp. 346-351;1996.

Chawla et al.; Radiotherapy and breast reconstruction: complications and cosmesis with tram versus tissue expander/implant; Int Jrnl Rad Onc Bio Phy; vol. 54; No. 2; pp. 520-526; 2002.

Chew et al.; Becker expander implants: truly a long term single stage reconstruction?; J Plastic Recontr & Aesthet Surg; vo. 63; pp. 1300-1304; 2010.

Christante et al.; Using complications associated with postmastectomy radiation and immediate breast reconstruction to improve surgical decision making; Arch Surg; vol. 145; No. 9; pp. 873-878; 2010.

Chun et al.; Implant-based breast reconstruction using acellular dermal matrix and the risk of postoperative complications; Plast Recontr Surg; vol. 125; No. 2; pp. 429-436; Feb. 2010.

Cohen et al.; Analysis of risks and aesthetics in a consecutive series of tissue expansion breast reconstructions; Plast Recontr Surg; vol. 89; No. 5; pp. 840-843; May 1992.

Collis et al.; Breast reconstruction by tissue expansion . . . ; Br J Plastic Surg; vol. 53; pp. 37-41; 2000.

(56) References Cited

OTHER PUBLICATIONS

Cordeiro et al.; A single surgeon's 12-year experience with tissue expander/implant breast reconstruction . . . ; Plast Recontr Surg; vol. 118; No. 4; pp. 832-839; Sep. 15, 2006.
Dickson et al.; The complications of tissue expansion in breast reconstruction: a review of 75 cases; Br J Plast Surg; vol. 40; pp. 629-635; 1987.
Disa et al.; The Premature Removal of Tissue Expanders in Breast Reconstruction; Plast Reconstr Surg; vol. 104; No. 6; pp. 1662-1665; Nov. 1999.
Edlich et al.; Advances in Breast Reconstruction After Mastectomy; J Long Term Eff Med Implants; vol. 15; No. 2; pp. 197-207; 2005.
Francis et al.; Independent Risk Factors for Infection in Tissue Expander Breast Reconstruction; Plast Reconstr Surg; vol. 124; No. 6; pp. 1790-1796; Dec. 2009.
Frankhouse et al.; Carbon Dioxide/Digital Subtraction Arteriography-Assisted Transluminal Angioplasty; Ann Vasc Surg; vol. 9; No. 5; pp. 448-452; 1995.
Gibney; The Long-Term Results of Tissue Expansion for Breast Reconstruction; Clinic Plastic Surg; vol. 14; No. 3; pp. 509-518; Jul. 1987.
Gibney; Use of a Permanent Tissue Expander for Breast Reconstruction; Plastic Reconstruct Surg; vol. 84; No. 4; pp. 607-617; Oct. 1989.
Gui et al.; Immediate Breast Reconstruction Using Biodimensional Anatomical Permanent Expander Implants . . . ; Plast Reconstr Surg; vol. 111; No. 1; pp. 125-138; Jan. 2003.
Haddock et al.; Breast Reconstruction with Implants, Tissue Expanders and AlloDerm . . . ; Breast J; vol. 16; No. 1; pp. 14-19; 2010.
Jhaveri et al.; Clinical Outcomes of Postmastectomy Radiation Therapy After Immediate Breast Reconstruction; J Radiat Oncol Biol Phys; vol. 72; No. 3; pp. 859-865; 2008.
Kronowitz; Delayed-Immediate Breast Reconstruction: Technical and Timing Considerations; Plast Recontr Surg; vol. 125; No. 2; pp. 463-474; Feb. 2010.
Krueger et al.; Complications and patient satisfaction following expander/implant breast reconstruction with and without radiotherapy; Int Jrnl Rad Onc Bio Phys; vol. 49; No. 3; pp. 713-721; 2001.
Lanier et al.; The Effect of Acellular Dermal Matrix Use on Complication Rates in Tissue Expander/Implant Breast Reconstruction; Ann Plast Surg; vol. 64; No. 5; pp. 674-678; May 2010.
Liu et al.; Does neoadjuvant chemotherapy for breast cancer increase complications during immediate breast reconstruction?; J Med Dent Sci; vol. 56; pp. 55-60; 2009.
Logan et al.; A Control Unit for Maximal Rate Continuous Tissue Expansion (CTE); Biomed Sci Instrum; vol. 25; pp. 27-33; 1989.
Losken et al.; Outcomes Evaluation Following Bilateral Breast Reconstruction Using Latissimus Dorsi Myocutaneous Flaps; Ann Plast Surg; vol. 65; No. 1; pp. 17-22; Jul. 2010.
Losken; Early Results Using Sterilized Acellular Human Dermis (NeoForm) in Postmastectomy Tissue Expander Breast Reconstruction; Plast Recontr Surg; vol. 123/ No. 6; pp. 1654-1658; Jun. 2009.
Machida et al.; Immediate v Chronic Tissue Expansion; Ann Plast Surg; vol. 26; No. 3; pp. 227-232; Mar. 1991.
Mahdi et al.; Expandable Anatomical Implants in Breast Reconstructions: A Prospective Study; Br J Plast Surg; vol. 51; pp. 425-430; 1998.
Marks; (Discussion) Comparison between rapid and slow tissue expansion in breast reconstruction; Plastic and Reconstructive Surgery; pp. 671-672; Apr. 1993.
Wickman; Comparison between rapid and slow tissue expansion in breast reconstruction; Plastic and Reconstructive Surgery; 91(4); pp. 663-670; Apr. 1993.
Maxwell et al.; Eighty-four consecutive breast reconstructions using a textured silicone tissue expander; Plastic and Reconstructive Surgery; vol. 89; No. 6; pp. 1022-1034; Jun. 1992.
May et al.; Smooth vs textured expander implants: a double-blind study of capsule quality and discomfort in simultaneous bilateral breast reconstruction patients; Ann Plast Surg; vol. 32; No. 3; pp. 225-233; Mar. 1994.

McCarthy et al.; Predicting complications following expander/implant breast reconstruction: an outcomes analysis based on preoperative clinical risk; Plast Reconstr Surg; vol. 121; No. 6; pp. 1886-1892; Jun. 2008.
Mitchell; Carbon dioxide flooding the operative field to minimize or prevent air embolism during open heart operations; Textbook of Extracorporeal Technology; 6 pgs.; 2003.
Mitchem et al.; Impact of neoadjuvant chemotherapy on rate of tissue expander/implant loss and progression to successful breast reconstruction following mastectomy; Am J Surg; vol. 196; pp. 519-522; 2008.
Mohmand et al.; Home Inflation of Tissue Expanders: A Safe and Reliable Alternative; Br J of Plast Surg; vol. 54; pp. 610-614; 2001.
Nahabedian et al.; Infectious Complications Following Breast Reconstruction with Expanders and Implants; Plast Reconstr Surg; vol. 112; No. 2; pp. 467-476; Aug. 2003.
Namnoum; Expander/Implant Reconstruction with AlloDerm: Recent Experience; Plast Reconstr Surg; vol. 124; No. 2; pp. 387-394; Aug. 2009.
Neumann; The expansion of an area of skin by progressive distention of a subcutaneous balloon; Plastic & Reconstructive Surgery; 19(2); pp. 124-130; Feb. 1957.
Nordstrom; Tissue Expansion; Butterworth-Heinemann (publishers); Chapters 8, 18, & 19; 2004.
Nunes et al.; Continuous expansion for the treatment of skin deformities; Aesth. Plast. Surg•; vol. 20; pp. 347-349; 1996.
Pusic et al.; An accelerated approach to tissue expansion for breast reconstruction: experience with intraoperative and rapid postoperative expansion in 370 reconstructions; Plastic and Reconstructive Surgery; vol. 3; No. 6; pp. 1871-1875; May 2003.
Pusic et al.; Clinical research in breast surgery: reduction and postmastectomy reconstruction; Clin Plas Surg; vol. 35; pp. 215-226; 2008.
Radovan; Breast reconstruction after mastectomy using the temporary expander; Plas Reconstr Surg; vol. 69; No. 2; pp. 195-206; Feb. 1982.
Revis; Tissue Expansion; emedicine (from WebMD); 14 pgs.; 2005.
Ronert et al.; The beginning of a new era in tissue expansion: self-filling osmotic tissue expander—four-year clinical experience; Plastic and Reconstructive Surgery; vol. 114; No. 5; pp. 1025-1031; Oct. 2004.
Saint-Cyr et al.; Use of the Serratus Anterior Fascia Flap for Expander Coverage in Breast Reconstruction; Plast Reconstr Surg; vol. 125; No. 4; pp. 1057-1064; Apr. 2010.
Sasaki; Interoperative Sustained Limited Expansion (ISLE) as an Immediate Reconstructive Technique; Clinic Plastic Surg; vol. 14; No. 3; pp. 563-573; Jul. 1987.
Sasaki; Intraoperative Expansion as an Immediate Reconstructive Technique; Facial Plastic Surg; vol. 5; No. 4; pp. 362-378; Jul. 1988.
Sasaki; Tissue Expansion in Reconstructive and Aesthetic Surgery; Mosby (publishers); pp. 190-192 and 206-242; 1998.
Sbitany et al.; Acellular Dermis-Assisted Prosthetic Breast Reconstruction versus Complete Submuscular Coverage: A Head-to-Head Comparison of Outcomes; Plast Reconstr Surg; vol. 124; No. 6; pp. 1735-1740; Dec. 2009.
Schmidt et al.; Continuous versus conventional tissue expansion: experimental verification of a new technique; Plast Reconstr Surg; vol. 87; No. 1; pp. 10-15; Jan. 1991.
Slavin et al.; Sixty consecutive breast reconstructions with the inflatable expander: a critical appraisal; Plast Reconstr Surg; vol. 86; No. 5; pp. 910-919; Nov. 1990.
Spear et al.; A retrospective analysis of outcomes using three common methods for immediate breast reconstruction; Plas Reconstr Surg; vol. 122; No. 2; pp. 340-347; Aug. 2008.
Spear et al.; Acellular Dermis-Assisted Breast Reconstruction; Aesthetic Plast Surg; vol. 32; pp. 418-425; 2008.
Spear et al.; Breast Reconstruction with Implants and Expanders; Plas Reconstr Surg; vol. 107; No. 1; pp. 177-187; Jan. 2001.
Spear et al.; Immediate breast reconstruction in two stages using textured, integrated-valve tissue expanders and breast implants . . . ; Plast Reconstr Surg; vol. 101; No. 1; pp. 53-63; Jan. 1998.

(56) References Cited

OTHER PUBLICATIONS

Spear et al.; Prophylactic mastectomy and reconstruction: clinical outcomes and patient satisfaction; Plas Reconstr Surg; vol. 122; No. 1; pp. 1-9; Jul. 2008.

Spear et al.; Prophylactic Mastectomy: Indications, Options, and Reconstructive Alternatives; Plast Reconstr Surg; vol. 115; No. 3; pp. 891-909; Mar. 2005.

Strock; Two-Stage Expander Implant Reconstruction: Recent Experience; Plast Reconstr Surg; col. 124; No. 5; pp. 1429-1436; Nov. 2009.

Sullivan et al.; True Incidence of All Complications following Immediate and Delayed Breast Reconstruction; Plas Reconstr Surg; vol. 122; No. 1; pp. 19-28; Jul. 2008.

Swart et al.; Breast Cancer; eMedicine; 54 pgs.; Dec. 17, 2010.

Tassan et al.; Tissue Expansion; Safr Med J; vol. 71; pp. 703-706; Jun. 6, 1987.

Tepper et al.; Three-dimensional imaging provides valuable clinical data to aid in unilateral tissue expander-implant breast reconstruction; Breast J; vol. 14; No. 6; pp. 543-550; 2008.

Toranto et al.; Endoscopic versus open tissue-expander placement: is less invasive better?; Plast Reconstr Surg; vol. 119; No. 3; pp. 894-906; Mar. 2007.

Trabulsy et al.; Changing trends in postmastectomy breast reconstruction: a 13-year experience; Plast Reconstr Surg; vol. 93; No. 7; pp. 1418-1427; Jun. 1994.

Youm et al.; Complications of tissue expansion in a public hospital; Ann Plast Surg; vol. 42; pp. 396-402; 1999.

Widgerow et al.; Patient-controlled expansion: applying a new technique to breast reconstruction; Aesth. Plast. Surg.; vol. 31; pp. 299-305; 2007.

Woods et al.; Breast reconstruction with tissue expanders: obtaining an optimal result; Ann Plast Surg; vol. 28; pp. 390-396; 1992.

Yanko-Arzi et al.; Breast Reconstruction: Complication Rate and Tissue Expander Type; Aesthetic Plast Surg; vol. 33; pp. 489-496; 2009.

\* cited by examiner

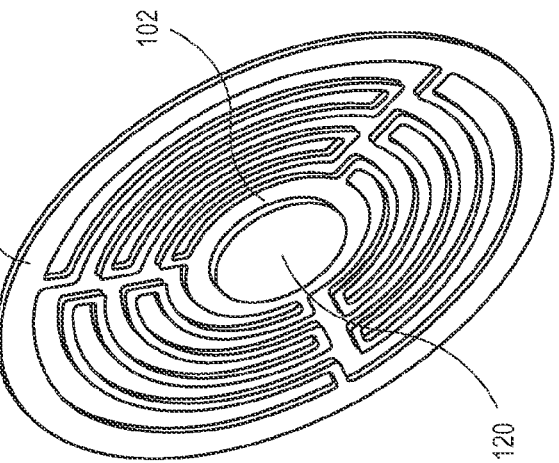
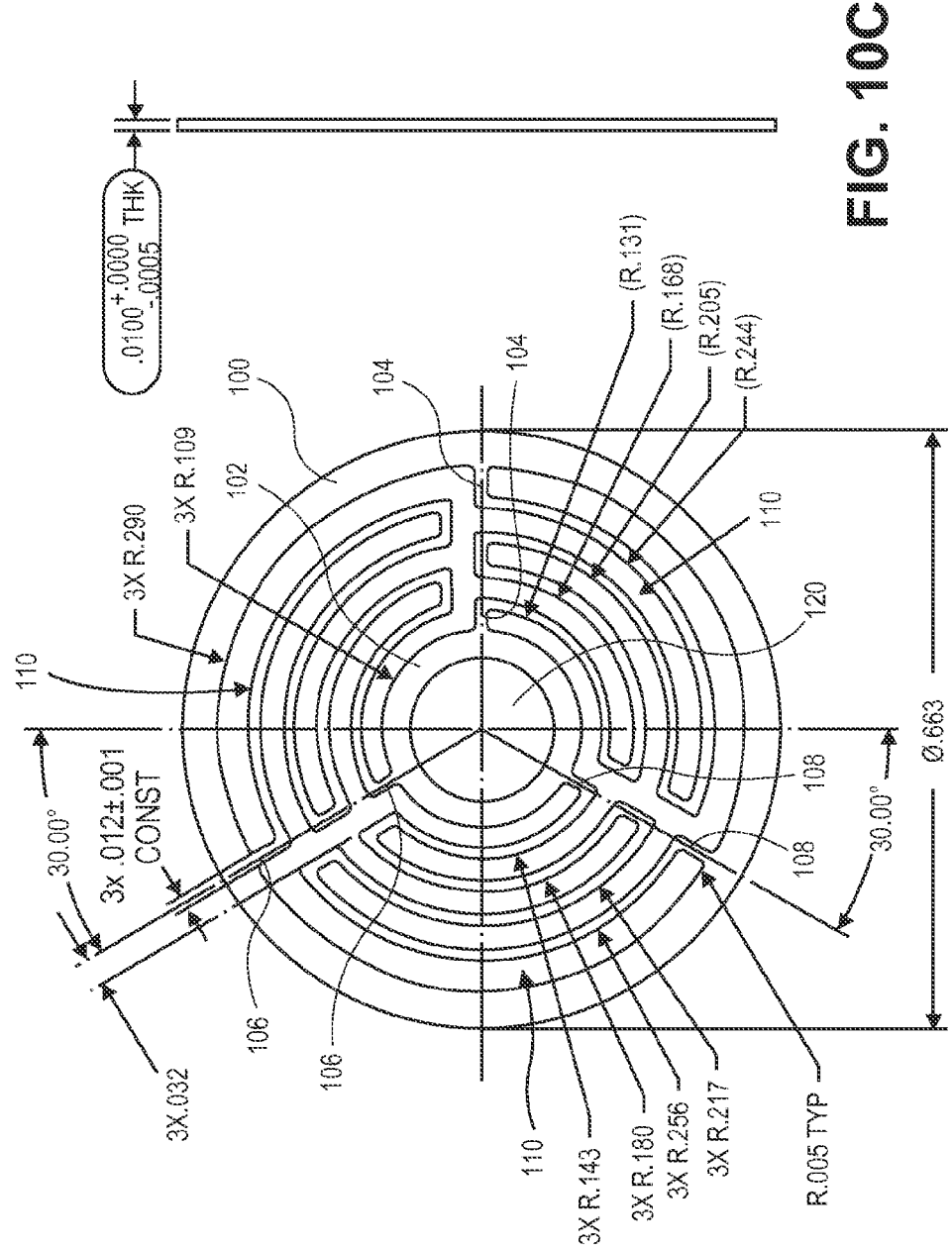
FIG. 10A   FIG. 10B   FIG. 10C

FIG. 13

Physician Quick Reference

1. Insert Key: Remove the Physician Master Key (PMK) from the Tissue Expander packaging, and place into slot at the end of the Dosage Controller (DC).
2. Sterile Prep: Remove Aseptic Transfer Pouch from the DC packaging, and place DC with PMK into pouch.
3. Implant/DC Bonding: Activate the DC by pushing the DC button through the sterile pouch to create a bond between the DC and the Tissue Expander.
4. Pre-Fill: Place DC over the Tissue Expander. When adequate signal strength is achieved, push the DC button again. Approximately 10cc of $CO_2$ will now be released. Repeat as desired. Partial filling prior to surgical placement is acceptable.
5. Implantation: Place Tissue Expander into surgical pocket with the loose fold facing inferiorly, and the antenna patch in the superior and anterior position. The horizontal $CO_2$ reservoir can assist with orientation.
6. Intraoperative Filling: After wound closure, fill Tissue Expander to tissue tolerance, eliminating 'dead space' and reducing the chance of seroma and/or hematoma.
7. Remove PMK and complete Patient Reference Card (PRC).
8. Set aside labeled DC and removed PMK for future use.

LS-0002 Rev. 4

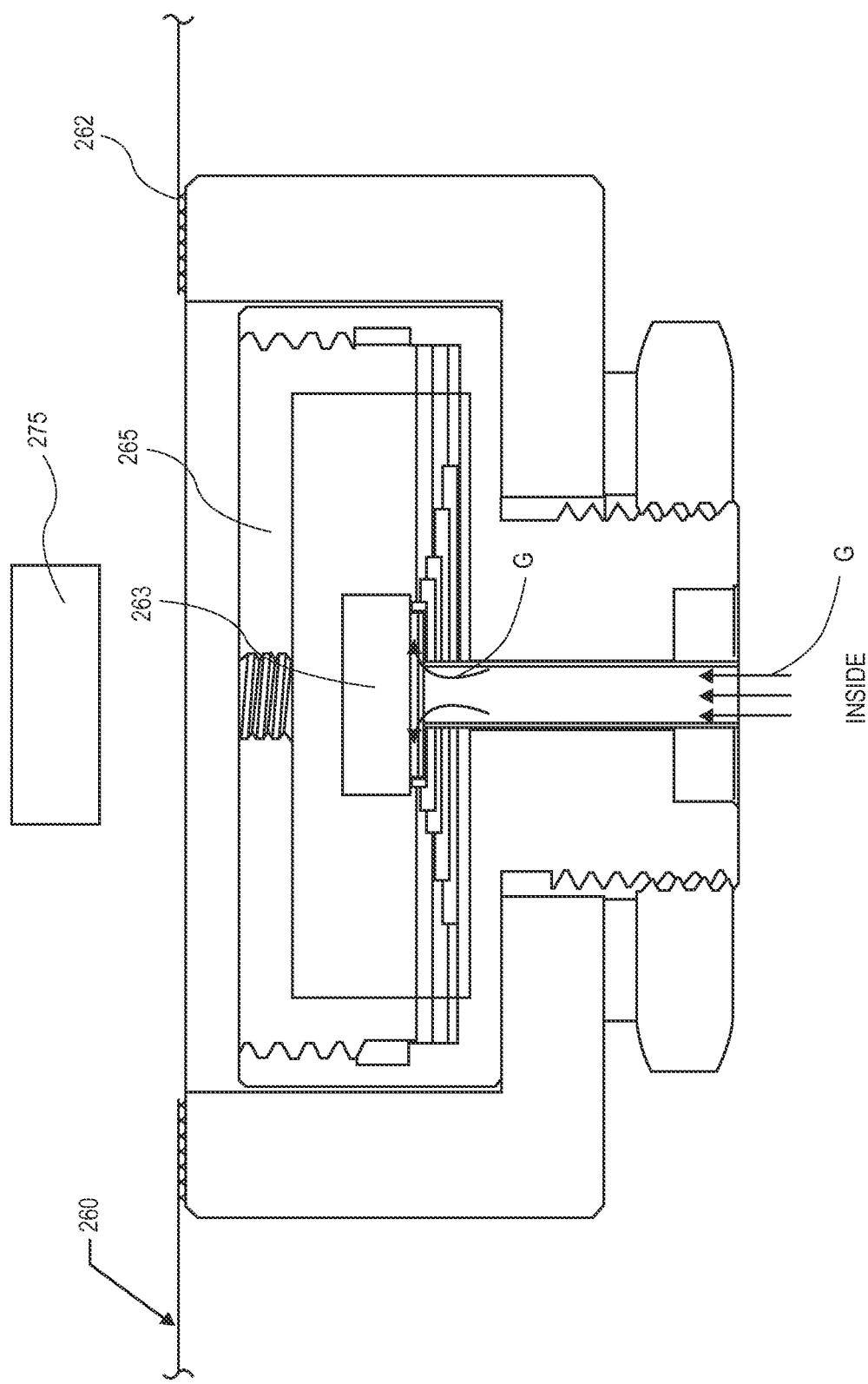

TISSUE EXPANDERS AND METHODS OF USE

CROSS-REFERENCE TO RELATED APPLICATIONS

This application is a continuation of pending U.S. application Ser. No. 12/973,693, filed Dec. 20, 2010; which claims the benefit of U.S. Provisional Application No. 61/288,197, filed Dec. 18, 2009; and Said U.S. application Ser. No. 12/973,693, filed Dec. 20, 2010, is also a continuation-in-part application of U.S. application Ser. No. 11/231,482, filed Sep. 21, 2005, which claims the benefit of U.S. Provisional Application No. 60/612,018, filed Sep. 21, 2004, and U.S. Provisional Application No. 60/688,964, filed Jun. 9, 2005.

All of the aforementioned applications are incorporated by reference herein.

INCORPORATION BY REFERENCE

All publications and patent applications mentioned in this specification are incorporated by reference herein to the same extent as if each individual publication or patent application was specifically and individually indicated to be incorporated by reference.

BACKGROUND

A deficit of normal tissue in a subject may result from, for example, burns, tumor resection surgery (e.g. mastectomy), or congenital deformities. Often, the tissue in deficit is skin and/or underlying connective tissue. The tissue in deficit can also be an intrabody duct (e.g. urethras or GI tract).

One method of correcting skin deficit is to stimulate creation of new skin. Implantation of a device that expands and stretches the existing skin causes a growth response in which new skin is created. While the exact physiologic mechanism of this response is not fully understood, clinical success has been reported for many years.

The formal concept of surgical tissue expansion was first reported by Neumann in 1957, in which a rubber balloon, attached to a percutaneous tube, was implanted to enable intermittent expansion for the purpose of reconstructing a partially amputated ear. The concept of tissue expansion was further refined and popularized for breast reconstruction by Radovan and Argenta in the 1980's. Despite many advantages of the technique, most notably minimal additional surgical dissection and patient downtime, the out-patient process remains lengthy and onerous, often involving months of weekly office visits and discomfort resulting from the relatively high pressures associated with periodic expansion by filling with saline. Most commercially available tissue expanders function as an implantable balloon with a separate or imbedded valve that allows periodic filling. Typically, a physician performs the filling procedure. The filling events are relatively infrequent (e.g., weekly), and therefore a significant expansion pressure is typically applied at each doctor's visit to achieve a maximum effect from each visit. As a result of this expansion pressure during a clinic visit, a relatively sudden tissue stretch occurs. This may cause subjects to suffer discomfort and/or tissue ischemia. The relatively large expansion pressure can also adversely affect underlying structures, such as causing concavities in underlying bone. In addition, high pressure may create restrictive capsules around the implant and/or cause tissue failure. Some previously available alternatives used a percutaneous needle for inflation or filling or inflation, creating a potential source of infection.

Gradual, continuous expansion was introduced and thought to overcome many of the drawbacks associated with periodic saline injections. For example, osmotic expanders have been reported by Austad in 1979, Berge in 1999, and Olbrisch in 2003 (see U.S. Pat. Nos. 5,005,591 and 5,496,368). A commercial version is available from Osmed Corp. in a limited range of sizes. These devices use a polymeric osmotic driver to expand a silicone implant by absorbing interstitial fluid ("ISF"). A potential problem of such devices is the lack of control or adjustability after implantation with respect to expansion variables such as pressure, volume, onset of expansion, and end of expansion once they have been deployed. U.S. Pat. No. 6,668,836 to Greenberg et al. describes a method for pulsatile expansion of tissue using an external hydraulic pump. The external hydraulic pump is bulky and inconvenient for patients. The percutaneous attachment reduces patient mobility and may be a source of contamination. U.S. Pat. No. 4,955,905 to Reed teaches an external monitor for pressure of an implanted fluid filled tissue expansion device. U.S. Pat. Nos. 5,092,348 and 5,525,275 to Dubrul and Iverson, respectively, teach implantable devices with textured surfaces. Some other devices use mechanical or electromechanical forces to avoid having to use fluids for tissue expansion.

Widgerow tested a continuous expansion device using an external pump connected through tubing to the implanted expander that allowed complete patient control. This provided rapid time courses and patient satisfaction. However, the connector tubing imparts both a cumbersome setup for the patient as well as the fear that prolonged connection between the external environment and the implanted device may lead to contamination. As the expanded space ultimately receives a permanent implant, any level of contamination is considered unacceptable.

Despite the advent and acceptance of breast conservation treatment modalities for breast cancer, mastectomy remains the treatment of choice for breast cancer in several clinical settings. These include situations in which there is an inability to achieve clean margins without unacceptable deformation of the remaining breast tissue, multiple primary tumors, previous chest wall irradiation, pregnancy, or severe collagen vascular diseases (e.g., lupus). Mastectomy is also indicated for women at high risk due to the presence of BRCA1 or BRCA2 or contralateral disease. Many such women are candidates for breast reconstruction and opt for reconstructive surgery at the time of mastectomy or in a delayed fashion after healing. According to the American Society of Plastic Surgery statistics, 57,102 U.S. patients underwent breast reconstruction in 2007.

Prosthetic reconstruction of the breast, as a staged procedure with tissue expanders followed by implants, is a reliable method for breast reconstruction that offers favorable aesthetic and psychological results while adding only minimal additional surgical intervention. Today, the process usually involves the placement of a tissue expander device under the pectoralis major muscle and remaining skin of the absent breast. The device is then gradually inflated over several weeks or months by periodic injections of saline, causing the stretching and expansion of the overlying skin and muscle coverage. When adequate coverage is achieved, the expansion device is typically removed, and a permanent breast implant is placed into the expanded space.

A significant clinical advantage would be realized if tissue expanders, such as breast tissue expanders, could provide any or all of the following: the elimination of technical problems associated with earlier devices while allowing greater patient comfort, control, speed, overall user friendliness, continuous or near continuous expansion, complete surgeon-patient control, and the eradication of percutaneous communication with the external environment which can lead to infection.

SUMMARY

One aspect of the disclosure is a tissue expansion system, including an implantable device adapted to be implanted within a patient, wherein the implantable device has an anterior portion, a posterior portion, an inferior portion, and a superior portion, and wherein the implantable device comprises a communication component secured in the superior and anterior portions, and an external device adapted to be disposed external to the patient to wirelessly communicate with the communication component to control the expansion of the implantable device.

In some embodiments the implantable device includes an inner layer defining an expandable chamber, wherein the inner layers comprises a preformed shape that defines the anterior, posterior, inferior, and superior portions, and wherein the communication component is secured to the superior and anterior portions of the inner layer. The inner layer can comprise an inelastic material. The inner layer can have a preformed general breast configuration defining the anterior, posterior, inferior, and superior portions, and wherein the communication component is secured to the anterior and superior portions of the general breast configuration. The general breast configuration can have a lower pole and an upper pole, wherein the upper pole is disposed in the superior portion, wherein the lower power has a thickness greater than a thickness of the upper pole, and wherein the communication component is secured within the upper pole.

In some embodiments the system further comprises a fluid reservoir within an inner chamber of the implantable device, wherein the communication component and the fluid reservoir are in communication, and wherein the external device is adapted to wirelessly communicate with the communication component to controllably release fluid from the fluid reservoir into the inner chamber. The communication component can include an antenna.

One aspect of the disclosure is a method of expanding tissue. The method includes an implantable device implanted with a patient, the implantable device comprising an expandable chamber, a fluid reservoir, and a communication component, positioning a remote controller proximate the bodily region in which the implantable device is implanted, and actuating the remote controller to expand a lower pole of the expandable chamber to have a greater projection than an upper pole of the expandable chamber. In some embodiments expanding the lower pole expands tissue adjacent the lower pole, and expanding the upper pole expands tissue adjacent the upper pole, and wherein expanding the lower pole to have a greater projection than the upper pole comprises expanding the tissue adjacent the lower pole to a greater extent than the tissue adjacent the upper pole. In some embodiments the expandable chamber has a preformed configuration in which the lower pole has a projection that is greater than a projection of the upper pole, and wherein actuating the remote controller expands the expandable chamber towards the preformed configuration. In some embodiments actuating the remote controller expands the expandable chamber towards a general breast configuration. In some embodiments the implantable device comprises anterior, posterior, superior, and inferior portions, and wherein positioning the remote controller proximate the bodily region in which the implantable device is implanted comprises positioning the remote controller adjacent the superior and anterior portions.

One aspect of the device is a breast implant that includes a self-contained implantable device adapted to be implanted within breast tissue of a patient, wherein the implantable device has a substantially inelastic portion having a general breast configuration.

In some embodiments the substantially inelastic portion comprises at least the curved portions of the general breast configuration. The substantially inelastic portion can additional comprise a generally flat posterior portion of the breast configuration. The anterior and posterior portions can be two different components secured together. In some embodiments the substantially inelastic portion at least partially defines an inner chamber in which a fluid is contained. In some embodiments the fluid is saline, and in some embodiments the fluid is a gas. In some embodiments the implant further comprises a gas reservoir disposed completely within the inner chamber. In some embodiments the implant further comprises a communication component disposed completely within the inner chamber adapted to wirelessly communicate with a device external to the patient. In some embodiments the external device is adapted to be actuated to control the release of gas from the gas reservoir into the inner chamber to expand the inner chamber. In some embodiments the general breast configuration includes an inferior portion and a superior portion, and wherein the inferior portion has a maximum projection dimension that is greater than a maximum projection dimension of the superior portion.

One aspect of the disclosure is a tissue expansion system including an implantable device comprising an expandable compartment and a gas source, wherein the gas source is secured within the expandable compartment but is not rigidly fixed relative to the expandable compartment to allow for relative movement between the gas source and the expandable compartment after the implantable component is positioned within a patient, and an external device adapted to control the release of gas from the gas source into the expandable compartment from a location external to the patient. In some embodiments the implantable device comprises a gas source retention element, at least a portion of which is fixedly secured to the expandable compartment, and wherein the gas source is secured to the expandable component using the gas source retention element. The gas source retention element can be a film layer, at least a portion of which is fixedly secured to the expandable compartment, and wherein the gas source is secured within the film layer. At least a portion of the gas source retention element can be fixed to a posterior portion of the expandable compartment. The gas source retention element and the gas source can form a hammock design.

One aspect of the disclosure is a tissue expansion system including an implantable device comprising a fluid source and an expandable chamber, an external controller adapted to wirelessly communicate with the implantable device to control the release of fluid from the fluid source into the expandable chamber to expand the expandable chamber, and a processing component adapted to compare the number of times fluid has been released from the fluid source within a given period of time with a maximum number of times fluid is allowed to be released from the fluid source within the given period of time. In some embodiments the processing component is disposed within the external controller. The processing component can be further adapted to prevent the release of fluid from the fluid source if the number of times fluid has been released from the fluid source within the given period of time is greater than or equal to the maximum number of times that fluid is allowed to be released from the fluid source within the given period of time. The processing component can be adapted to prevent the fluid source from releasing fluid more than 3 times within about a 24 hour period. The processing component can be adapted to prevent the fluid source from releasing fluid more than once about every 3 hours.

In some embodiments the external controller is adapted to communicate with the implantable device upon actuation of the external controller to control the release of fluid from the fluid source, and wherein the processing component is adapted to compare the number of times the external controller has been actuated within a given period of time with a maximum number of times the external controller can be actuated within the given period of time. The fluid source can be a compressed gas source.

One aspect of the disclosure is a tissue expansion system, including an implantable device comprising a gas source and an expandable chamber, an external controller adapted to wirelessly communicate with the implantable device to control the release of fluid from the fluid source into the expandable chamber to expand the expandable chamber, and a processing component adapted to compare the volume of fluid that has been released from the fluid source within a given period of time with a maximum volume of fluid that is allowed to be released from the fluid source within the given period of time.

In some embodiments the processing component is disposed within the external controller. The processing component can be further adapted to prevent the release of fluid from the fluid source if the volume of fluid that has been released from the fluid source within the given period of time is greater than or equal to the maximum volume of fluid that is allowed to be released from the fluid source within the given period of time. The processing component can be adapted to prevent the fluid source from releasing more than about 30 mL of fluid within about 24 hours. In some embodiments the fluid source is a compressed gas source.

One aspect of the disclosure is a tissue expansion system including an implantable device comprising a fluid source and an expandable chamber, an external controller adapted to wirelessly communicate with the implantable device in response to actuation of the external controller to control the release of fluid from the fluid source into the expandable chamber to expand the expandable chamber, and a processing component adapted to prevent more than a maximum volume of fluid from being released from the fluid source upon a single actuation of the external controller. In some embodiments the processing component is disposed within the external controller. The processing component can be adapted to prevent more than about 10 mL of fluid from being released upon a single actuation of the external controller. The system can include a memory component that logs an event if more than the maximum volume of fluid is released from the fluid source upon a single actuation of the external controller.

One aspect of the disclosure is a tissue expansion system, including an implantable device comprising a fluid source and an expandable chamber, an external controller adapted to wirelessly communicate with the implantable device to control the release of fluid from the fluid source into the expandable chamber to expand the expandable chamber, and a processing component adapted to compare the total volume of fluid released from the fluid source into the expandable chamber with a maximum fill volume for the implantable device. In some embodiments the fluid source is a gas source. The processing component can be disposed within the external controller. The processing component can be further adapted to prevent the release of fluid from the fluid source if the total volume of fluid that has been released from the fluid source is greater than or equal to the maximum fill volume for the implantable device. The processing assembly can be adapted to prevent the release of fluid from the fluid source if a total of about 350 mL to about 1040 mL of fluid has been released from the fluid source.

One aspect of the disclosure is a tissue expansion system including an implantable device comprising a fluid source and an expandable chamber, an external controller adapted to wirelessly communicate with the implantable device to control the release of fluid from the fluid source into the expandable chamber to expand the expandable chamber, and a processing component adapted to compare a total volume of fluid released from the fluid source into the expandable chamber with a maximum fill volume for the implantable component, wherein the processing component is adapted to automatically adjust the total volume of fluid released from the gas source into the expandable chamber to account for a volume of fluid that has permeated out of the expandable chamber.

In some embodiments the fluid source is a compressed carbon dioxide ($CO_2$) reservoir, and the processing component is adapted to automatically adjust the total volume of carbon dioxide released from the carbon dioxide reservoir into the expandable chamber to account for a volume of carbon dioxide that has permeated out of the expandable chamber. The processing component can be adapted to automatically cause the release of fluid from the fluid source to compensate for the volume of fluid that has permeated out of the expander chamber.

One aspect of the disclosure is a tissue expansion system including an implantable device comprising a gas source, an expandable chamber, and a pressure relief valve adapted to release gas from the expandable chamber, and an external controller adapted to communicate with the implantable device to control the release of gas from the gas source into the expandable chamber to expand the expandable chamber. In some embodiments the external controller comprises an actuator that is adapted to open the relief valve upon actuation thereof to release gas from the expandable chamber. The external controller can comprise a second actuator that is adapted to be actuated by control the release of gas from the gas source. The implantable device can comprise a pressure sensor adapted to sense when the pressure within the expandable chamber exceeds a maximum allowable pressure, and wherein the pressure relief valve is adapted to automatically open to release a volume of gas from the expandable chamber. The external controller can comprise a pressure sensor adapted to sense when the pressure within the expandable component exceeds a maximum allowable pressure. The pressure relief valve can comprise a first magnetic component, and wherein the system further comprises relief valve actuator comprising a second magnetic component, wherein the second magnetic component is adapted to interact with the first magnetic component to open the relief valve and release gas from the expandable chamber.

One aspect of the disclosure is a tissue expansion system including an implantable device comprising a fluid source, an expandable chamber, and an intrinsic port, wherein the fluid source is in fluid communication with the expandable chamber, and an external controller adapted to wirelessly communicate with the implantable device to control the release of fluid from the fluid source into the expandable chamber to expand the expandable chamber, wherein the intrinsic port is adapted to allow a removal device to be inserted therethrough to remove fluid from the expandable chamber. In some embodiments the removal device is a needle, and the intrinsic port is adapted to re-seal after the needle is inserted therethrough to remove fluid from the expandable chamber. The intrinsic port can be adapted to allow the implantable device to be re-filled with a second fluid, such as saline, after the fluid is released from the expandable chamber. The external controller can be adapted to wirelessly communicate with the implantable device to control the release of fluid from the fluid source after the removal of the fluid from the expandable chamber. The implantable device can further comprise a communication component, and wherein the instrinsic fill port is disposed adjacent the communication component. The implantable device can comprise an outer shell and an inner bag, wherein the intrinsic port is formed in the outer shell. The implantable device can comprise an outer shell and an inner bag, wherein the intrinsic port is disposed within the inner bag.

One aspect of the disclosure is a method of removing fluid from an implant, including removing a gas from a self-contained implant positioned within breast tissue, wherein removing the fluid comprises advancing a needle through an intrinsic port within the self-contained implant and removing fluid through the needle, and after a radiation therapy has been performed on the patient, re-filling the self-contained implant with a second fluid. The second fluid can be saline. Re-filling the self-contained implant with a second fluid can comprise positioning a needle through the intrinsic port and advancing the second fluid through the needle and into the implant.

BRIEF DESCRIPTION OF THE DRAWINGS

FIGS. 10A-C illustrate an exemplary magnetic enhancement pad incorporated into a valve spring.

FIGS. 13 and 14 show an exemplary physician quick reference and a patient quick reference for using exemplary expansion systems.

FIGS. 16 and 17 show an exemplary embodiment of a pressure relief valve that can be incorporated into a tissue expansion system.

DETAILED DESCRIPTION

The disclosure herein relates to tissue expanders and methods of using tissue expanders. In some embodiments the tissue expanders are used to expand breast tissue, but the tissue expanders can be used to expand tissue in other areas of the body. In some embodiments a tissue expansion system includes an implantable assembly, or implant, and a remote controller, which is adapted to remain external to the patient and can be actuated by the patient to wirelessly control the expansion of the implantable portion. Expansion of the implantable portion causes the expansion of tissue in the region of the body in which the implantable portion is positioned.

Figure 1:
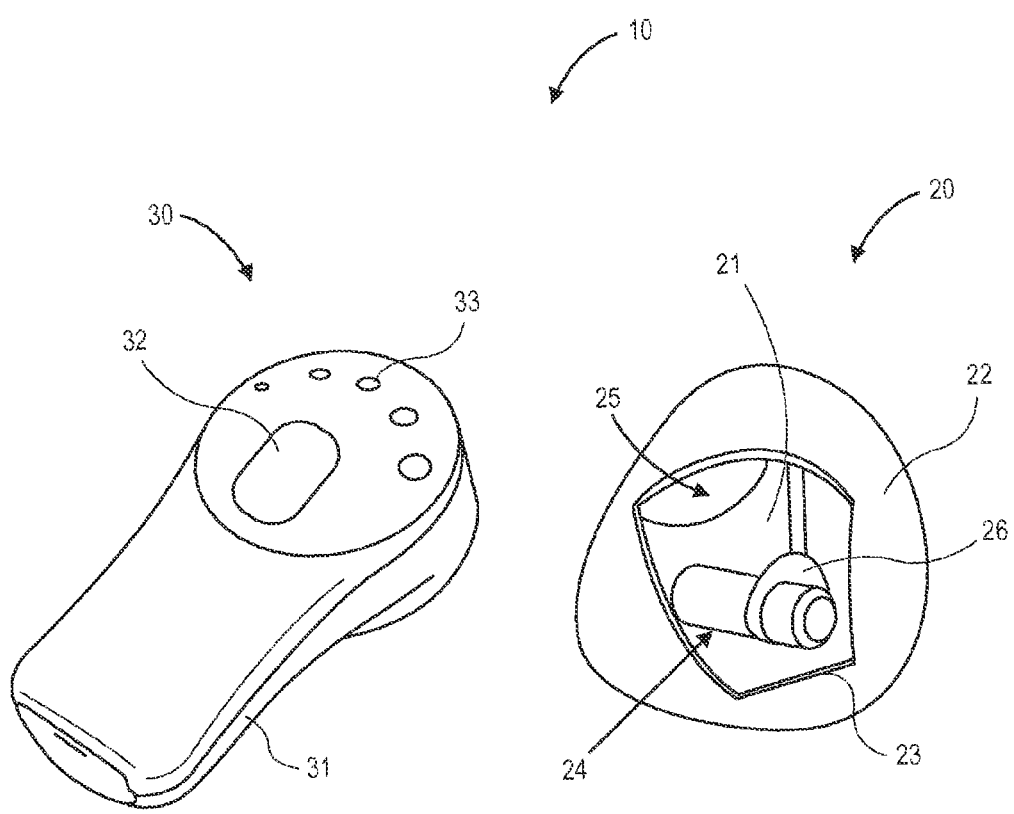
FIG. 1 shows an exemplary tissue expansion system including an implantable device and a remote controller.

FIG. 1 illustrates an exemplary embodiment of a tissue expansion system. Tissue expansion system 10 includes implantable portion 20 (also referred to herein as "implant") and remote controller 30. In this embodiment the implantable portion has a general breast shape or configuration and is adapted for breast reconstruction following, for example, mastectomy. Implantable portion 20 includes outer shell 22 and an inner bag, which comprises anterior portion 23 and posterior portion 21. A portion of the outer shell and the anterior portion of the inner bag are shown removed to illustrate additional components of the implant. The inner bag defines an expandable inner chamber, or compartment. Implant 20 also includes fluid reservoir and valve 24 (when combined are commonly referred to herein as a "driver"), as well as communication component 25. The driver and the communication component are positioned completely within the inner bag and secured thereto, either directly or indirectly. In FIG. 1, driver 24 is secured to cradle 26, which is secured to posterior portion 21 of the inner bag.

Tissue expansion system 10 also includes remote controller 30, which is generally adapted to wirelessly communicate with and provide power to the implantable portion via communication device 25 to control the release of fluid from the fluid reservoir into the expandable inner chamber. Remote controller includes housing 31, actuator 32, and output 33. Actuator 32 is shown as an actuatable button, while output 33 is shown as a plurality of visual indicators (e.g., LEDs). The actuator in the remote controller can be any other suitable actuator (e.g., a knob, a microphone adapted to receive a user's voice as input, etc.). The output can provide any number of different types of output to communicate information, such as, for example, visual, audio, tactile, etc.

Figure 2:
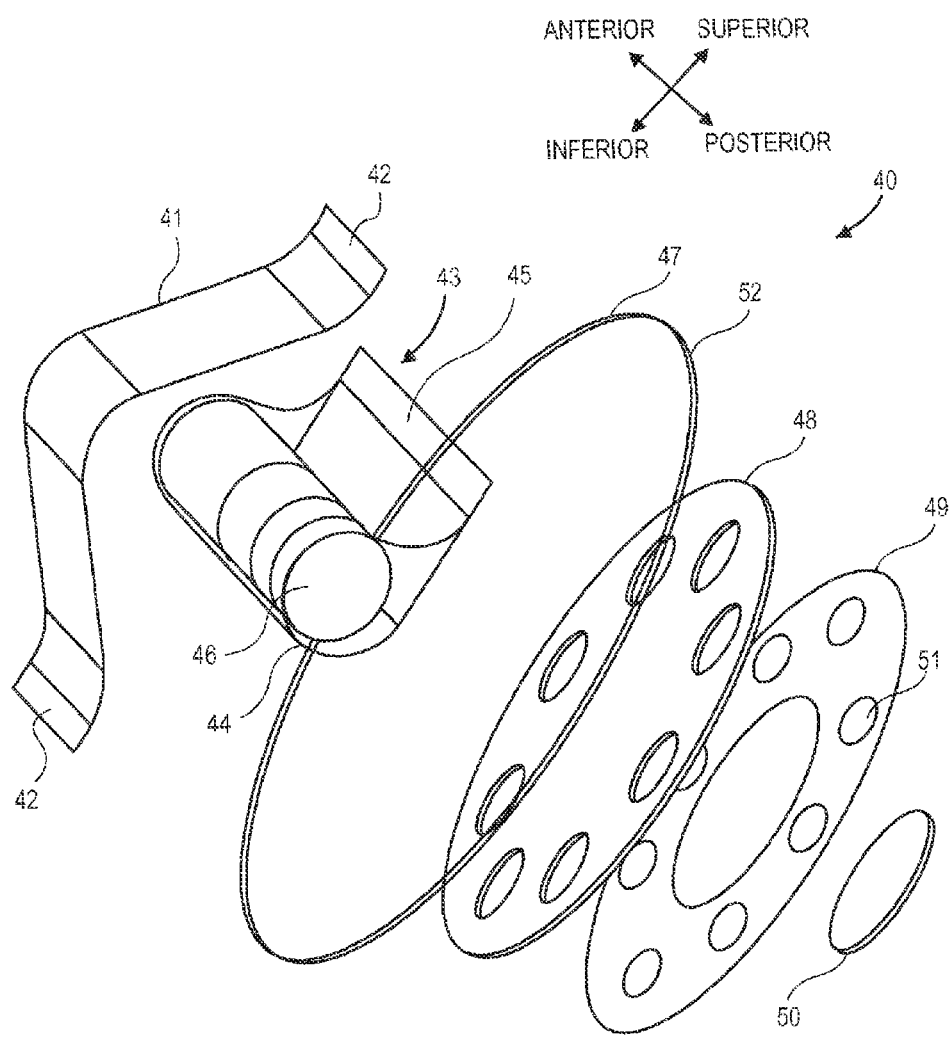
FIGS. 2 and 3 illustrate a portion of an exemplary implantable device in which the fluid source is not rigidly fixed to the expandable compartment.
Figure 3:
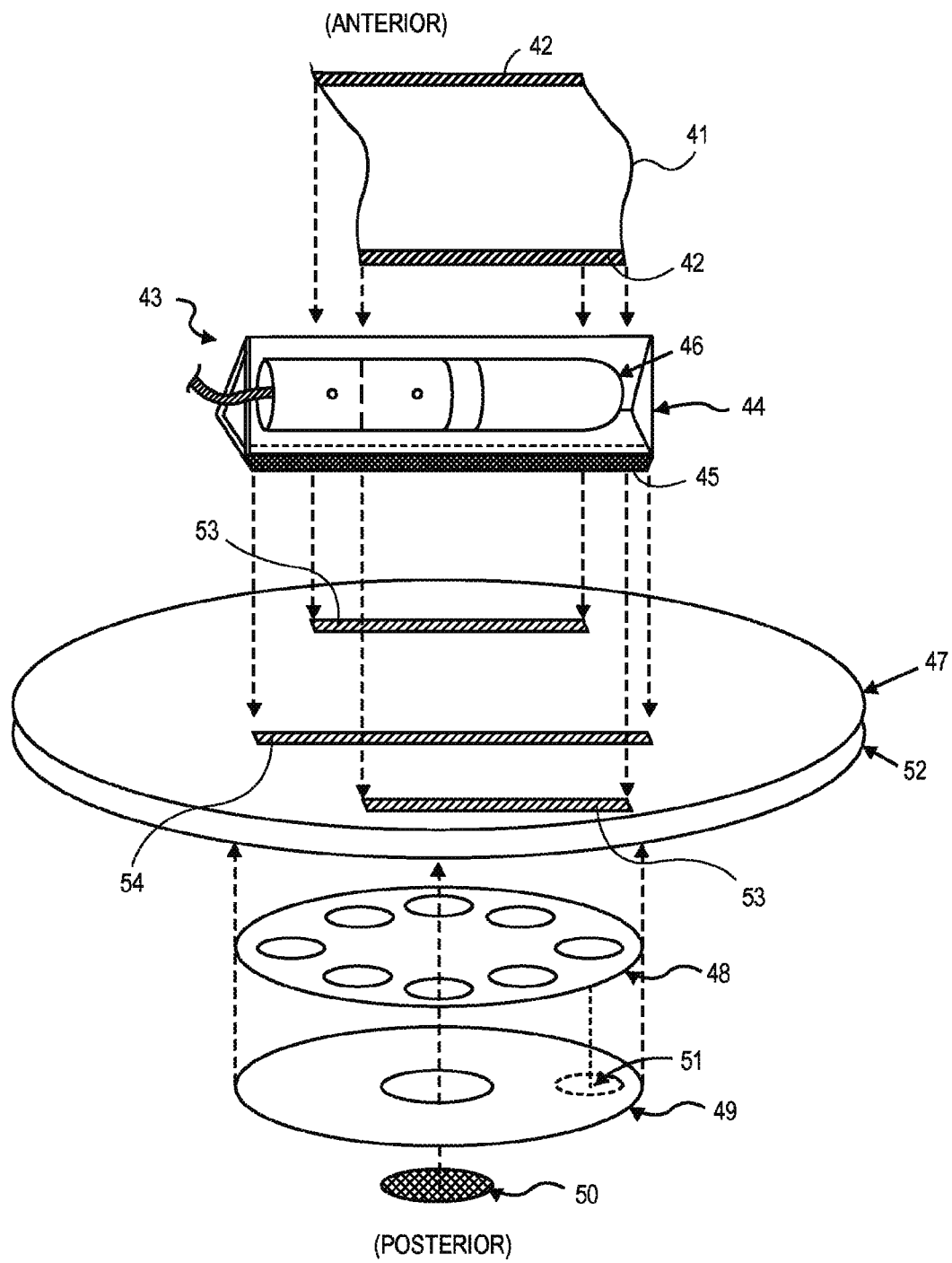

FIGS. 2-3 illustrate exploded views of a portion of an alternative embodiment of an implantable portion. FIG. 3 illustrates in greater detail the alignment of the components of the assembly. FIG. 2 illustrates generally the posterior portion of the inner bag and the manner in which the driver is secured thereto. The portion of implant 40 illustrates a general "hammock" design which allows the driver to be secured to the implant but where it is not rigidly fixed to the expandable chamber. This design provides for a greater degree of movement between the driver and the inner bag. The embodiment in FIG. 2 also reduces the "height," or projection of the driver in the anterior direction. The portion of the implant shown includes film band 41, hammock 43, driver 46, posterior panel barrier film 47, posterior panel 52, sheeting material 48, barrier ring 49, and outer patch 50. In a merely exemplary embodiment, the components are made of the following materials: film band 41 is a polyethylene film; hammock 43, which includes film 44, is a polyethylene film, posterior panel barrier film 47 is a polyethylene/polyvinylidene chloride ("PVDC") film; sheeting material 48 is a textured silicone material; barrier ring 49 is a polyethylene/PVDC film; and outer patch 50 is a silicone material.

In an exemplary assembly of the implant shown, ends 42 of film band 41 are heat-staked to posterior panel barrier film 47 at seal areas 53 (shown in FIG. 3). Seal area 45 of film 44 is heat-staked to posterior panel barrier film 47 at seal area 54. The heat-staking secures hammock 43 to posterior panel barrier film 47. End 45 of hammock 43 is superiorly positioned to allow driver 46 to "hang" within hammock 43. Barrier ring 49 is heat-staked to posterior panel 52 at the eight (8) seal areas 51 (only one is shown in FIG. 3), which secures silicon sheeting material 48 between barrier ring 49 and posterior panel 52. Outer patch 50 is secured to sheeting material 48 using silicone adhesive. Once assembled the portion of the implant 40 can then be secured to the rest of the implant (e.g., the anterior portion of the inner bag and the outer shell).

In the embodiment shown in FIGS. 2 and 3, the height, or projection, of the driver is reduced. Because the driver is not rigidly fixed to the inner expandable compartment, it has more flexibility within the implant. The position of the driver can be slightly adjusted relative to parts of the anatomy to relieve discomfort caused by the driver. For example, the driver can pivot, or rock, if it is located on top of a bony rib, thereby reducing discomfort to the patient. This arrangement allows the driver to be secured to the expandable chamber without being rigidly fixed thereto. While this design does provide for movement of the driver within the implant, film band 41 acts to prevent the driver from moving around too much due to patient movement (e.g., jumping, driving over bumpy terrain, etc.).

Figure 4:
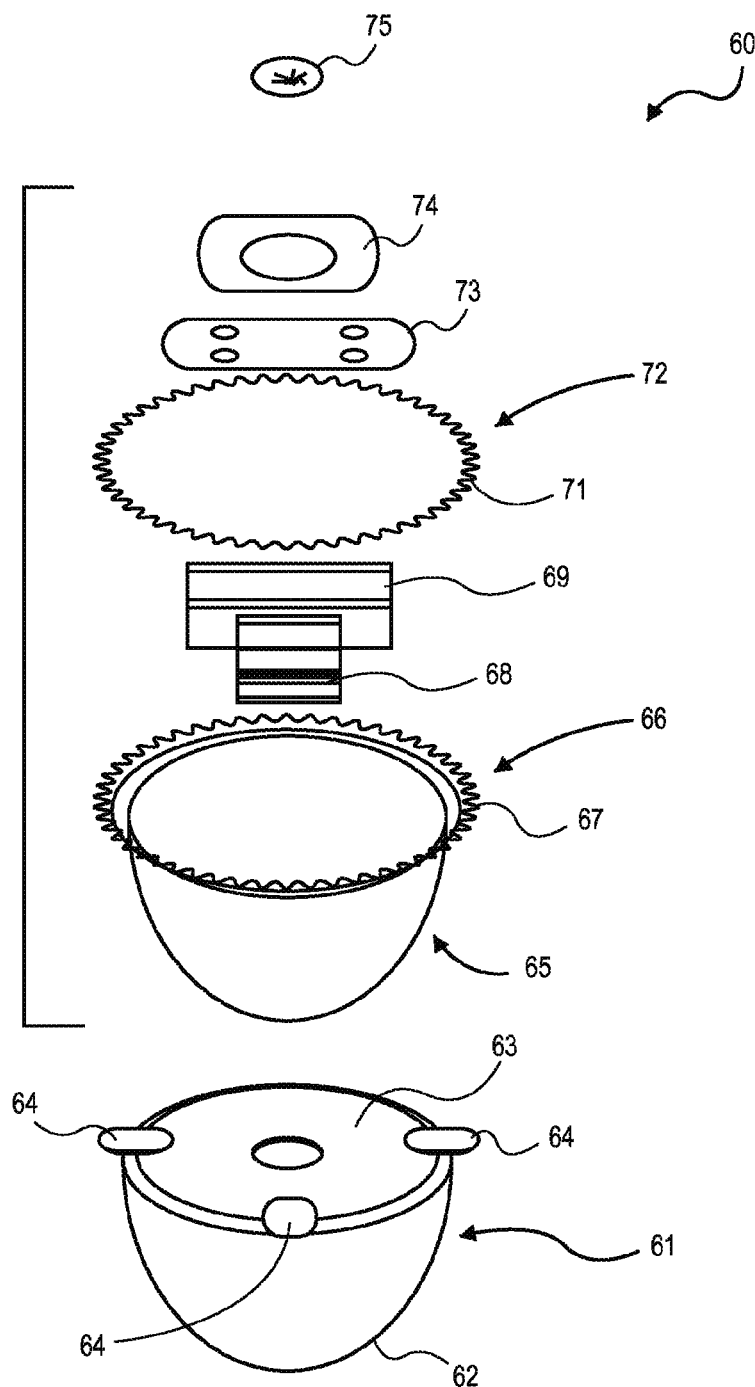
FIG. 4 illustrates an exploded view of a portion of an exemplary implantable device.

FIG. 4 illustrates an alternative embodiment of an implantable portion (driver and implant antenna not shown). The inner bag includes generally breast-shaped anterior portion 65, which has a perimeter seal 66 with a serpentine cut that creates a plurality of fingers 67. The inner bag also includes posterior portion 72, which also has a serpentine cut around a perimeter seal to create a plurality of fingers 71. In an exemplary method of manufacturing, phone dial film 74 is heat staked to posterior portion 72 through phone dial 73. Hammock 69 and band 68 are heat staked to the inner surface of posterior portion 72 as in the embodiment in FIGS. 2 and 3. The perimeter of anterior portion 65 is heat staked to the perimeter of posterior portion 72, forming the inner expandable chamber. The inner bag, once assembled, is then placed within outer shell 61, which comprises anterior portion 62 and posterior portion 63. Anterior portion 62 and posterior portion 63 can be integral, or they can be separate components secured together. Identifier 75, which can include information identifying the implant, is secured to phone dial 73 after the inner bag is placed within shell 61. The implant also optionally includes at least one suture tab 64, which can be used to help secure the implant to tissue within the subject. Sutures can be used to secure the suture tabs to tissue within the patient, thereby securing the implant within the patient. The suture tabs 64 can be secured to the implant after assembly with adhesive, such as silicon adhesive.

In some embodiments the perimeter formed when the perimeters of anterior portion 65 and posterior portion 72 are heat staked together can become rigid and may cause discomfort when implanted. The embodiment in FIG. 4 includes serpentine cuts in the perimeters of both anterior portion 65 and posterior portion 72, which create the fingers described above, to reduce the amount of rigidity in this region. In some embodiments all of the fingers are heat staked together, while in some embodiments less than all of the fingers are heat staked. In some embodiments at least one of the fingers is cut off or trimmed to reduce the stiffness of the finger region.

In one or more exemplary embodiments, the components of the implantable portion can be made from the following materials: the outer shell comprises silicone rubber; the suture tabs comprise silicone rubber with polyester (Dacron) reinforcement; the inner bag is a barrier film; the hammock and the band are either polyethylene or barrier film; and the phone dial and the phone dial film are silicone rubber.

Figure 5:
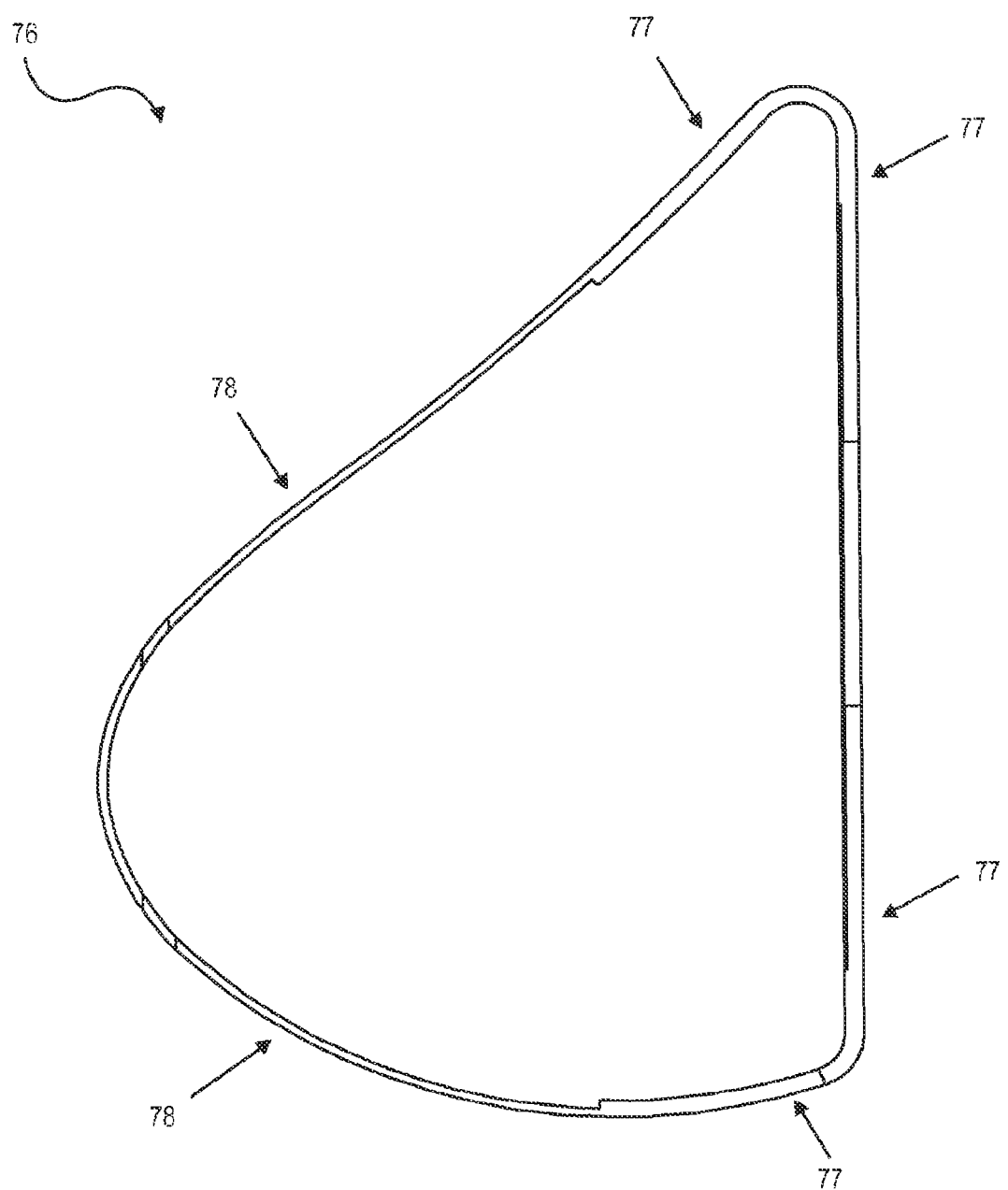
FIG. 5 illustrates an exemplary outer shell in which portion of the shell have a greater thickness than other portions of the shell.

FIG. 5 illustrates an alternative outer shell wherein a portion of the shell is thicker than other portions of the shell. Shell 76, into which an inner bag is to be placed (see FIG. 4), is thicker in regions 77 than in regions 78. The thicker regions 77 include the posterior backing of the shell and regions adjacent to the posterior backing. The thickened regions provide protection for the patient from the fingers (see FIG. 4), which can be slightly rigid and cause discomfort when the implant is implanted. The shell can be adapted to be thicker is additional regions as well if there are any other components associated with the inner bag that may provide discomfort to the patient.

In the embodiments in which the fluid is $CO_2$, the inner bag provides a barrier to $CO_2$ after it has been released from the gas reservoir.

In some embodiments the inner bag or chamber is non-elastic and is pre-formed in an anatomical shape, such as, for example without limitation, a breast. The inner chamber will expand to the anatomical shape when the fluid is released from the reservoir into the internal chamber. This responds unlike a liquid-filled elastomeric balloon, which does not have a preformed shape to which the balloon expands when filled with a liquid. When the inner bag has a preformed shape of a breast, the expanded shape emphasizes lower pole expansion where tissue generation is particularly desired during breast reconstruction so that the skin assumes the shape of a breast. FIGS. 1 and 4 are exemplary embodiments in which a substantially inelastic portion of the implant has a breast configuration or shape. In particular, in these embodiments the inner chamber is the inelastic component that has the general breast shape.

In some embodiments the inner bag comprises multiple layers of material that are sandwiched together to form the inner bag. Exemplary materials which may be utilized in the inner bag can be found in U.S. Pat. App. Pub. 2006/0069403, filed Sep. 21, 2005, which is incorporated herein by reference. In some embodiments the inner bag roughly has the thickness of a piece of paper, and while it has the ability to stretch a relatively small amount, it does not have properties like an elastic film. To form the inner bag in the desired anatomical shape, any layers which make up the inner bag are positioned adjacent one another with the desired layering, heated, applied to a mold which has the desired shape, and then allowed to cool on the mold. The mold is then removed. In the embodiment in FIG. 4, for example, any layers that make up anterior portion 85 can be formed on a mold as described above.

Using a non-elastic inner layer also prevents the implant from expanding into undesirable shapes since the inner bag will tend to expand into its pre-formed shape. This is unlike, for example, a hot-dog shaped elastomeric balloon, which, if squeezed in the middle, will become a dog-bone shaped balloon. Forming the inner bag in the shape of a breast, for example, prevents the implant from expanding laterally (under an arm) or superiorly (toward the clavicle). The shape of the tissue to be expanded can therefore be controlled by forming the inner bag into a particular shape.

In some embodiments the fluid source is a gas source, and in some embodiments the gas is, for example without limitation, $CO_2$. In some embodiments the gas reservoir has an internal volume of about 1 cc to about 50 cc, and in some embodiments is about 2 cc to about 10 cc. In an exemplary embodiment, a compressed gas source has a total internal volume of about 5 ml. Optionally a large tissue expansion may be achieved by providing about 2.5 grams of $CO_2$ in a 5 ml internal-volume container. This provides about 1200 ml of $CO_2$ at 15.5 PSI (0.8 PSI above atmosphere at sea level). The exact amounts may vary, but in some embodiments a constant ratio can be used. For example, for every 1 mL of internal volume container filled with 0.5 grams of $CO_2$ gas, there is about 240 mL final volume (at 0.8 PSI). The reservoir can be encased in a leak-free canister.

The outer shell generally provides a tissue interface for the implantable device. In some embodiments the outer shell is comprised of silicone, but can be made of any other suitable material. It can be smooth, but in some embodiments the outer shell is textured to help stabilize the implant within the patient. When the outer shell is a silicone outer shell, the silicone outer shell provides little resistance to the permeation of $CO_2$.

The implantable portion of the tissue expansion system includes a communication component, which can include an antenna, to facilitate communication with the remote controller. In some embodiments the communications component is secured to an anterior portion of the inner bag to provide for the easiest coupling between the remote controller and the antenna when the remote controller is held close to the patient's body in the region in which the implant is positioned. For example, in the embodiment in FIG. 1, communications component 25 is secured to the anterior portion of the inner bag. Communications component 25 is also secured to a superior portion of the inner bag, which can make it easier for the remote controller to communicate with the communications portion of the implant.

Figure 5A:
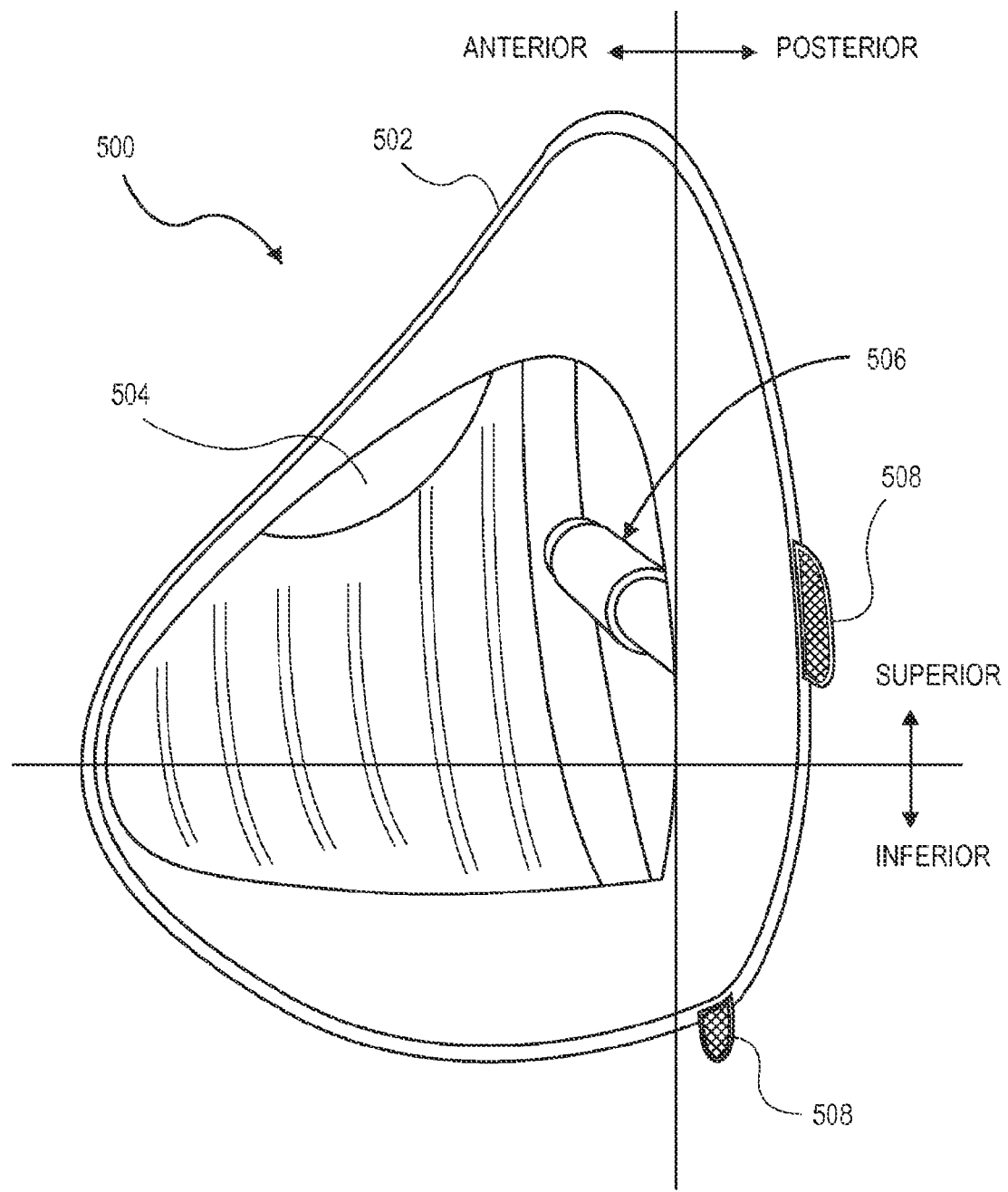
FIG. 5A illustrates an exemplary implantable device with a general breast-shaped expandable compartment.

FIG. 5A illustrates an exemplary implant 500, which includes inner bag 502 (outer shell not shown) with a section removed to reveal communications component 504 and driver 506, both of which are secured to inner bag 502. Implant 500 also includes suture tabs 508 (a third tab is not shown). In general, the inner bag has anterior and posterior portions as indicated. In this embodiment, the posterior portion generally refers only to the backing, or the generally flat portion, of the inner bag. The curved portions of the inner bag are generally considered the anterior portion. Additionally, the inner bag has an inferior portion and a superior portion as shown. The implant can be considered to be divided into 4 quadrants, based on the planes separating the anterior/posterior portions and the superior/inferior portions. As shown, the antenna is secured to the anterior portion and the superior portion of the inner bag to make the coupling between the remote controller (not shown) and communication component 504 as efficient as possible.

In embodiments in which the inner bag has a preformed expanded configuration, the communication component is attached to a complex 3-dimensional shape in which the inner bag is formed. The communication component, however, has the ability to deform the shape of the inner bag when secured thereto due to the weight and stiffness of the communication component. In some embodiments, in order to secure the communication component to the inner bag without altering the shape of the inner bag, the communication component is first encapsulated in a film layer, which is then secured to the inner bag. During attachment of the encapsulated communication component, the formed membrane has the ability to provide an approximately uniform amount of pressure over the communication component while it is attached to the inner bag. A material such as an ESCAL™ bag can be used as the membrane to provide the necessary amount of pressure to the encapsulated communication component while being laminated to the inner bag. This will prevent the inner bag from losing its preformed shape. Additionally, the communication component is positioned on the anterior portion of the inner bag to maintain its position as close as possible to the surface of the patient. This improves the communication component's electromagnetic coupling with the remote controller.

Figure 6:
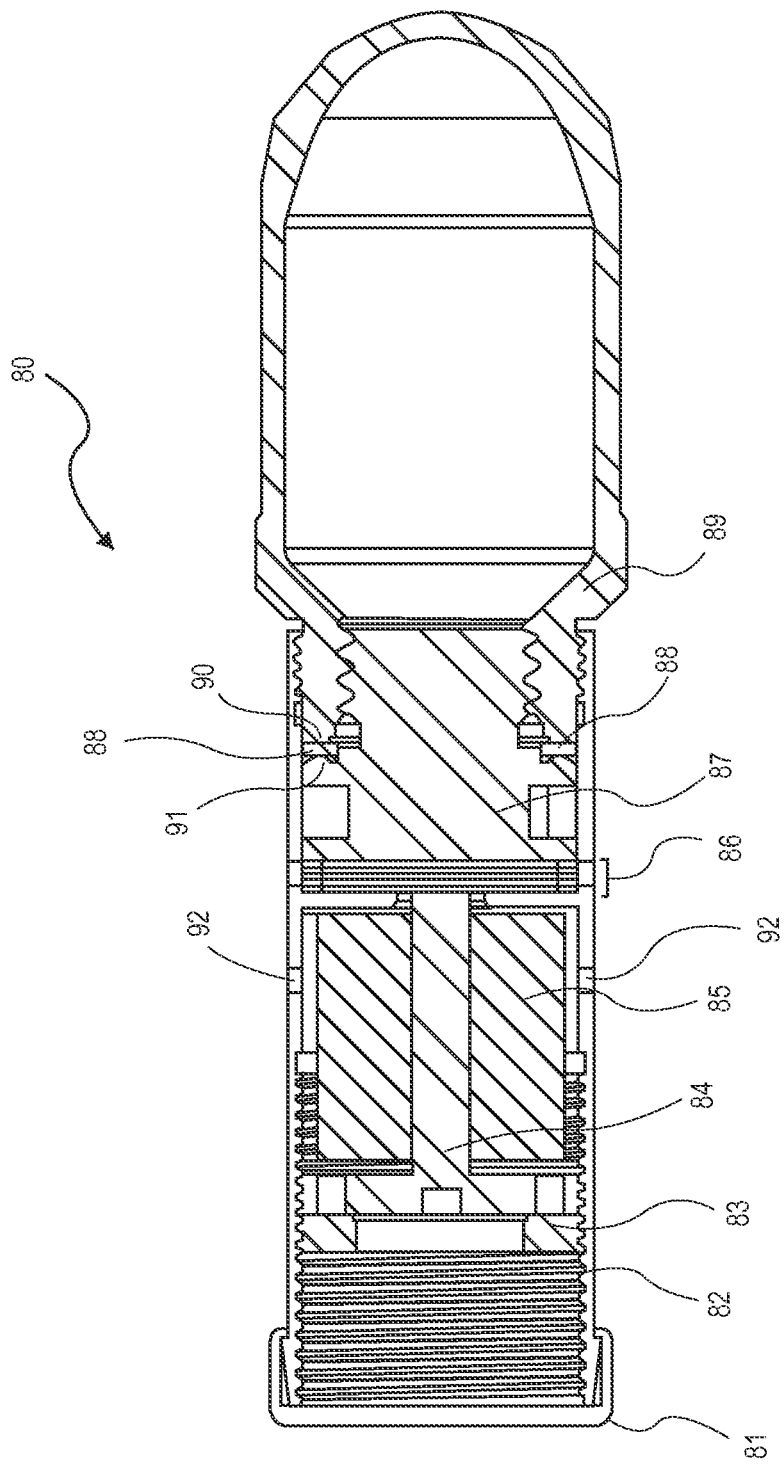
FIG. 6 illustrates an exemplary driver.

The implant also includes a driver, which comprises a fluid reservoir and a valve, which controls the flow of fluid from the reservoir. In some embodiments the fluid reservoir is a compressed gas source. Actuation of the remote controller can open the valve to controllably releases gas from the reservoir into the inner chamber. In some embodiments the valve is a solenoid valve. FIG. 6 illustrates a side cross-sectional view of an exemplary driver. Driver 80 includes $CO_2$ canister 89 screwed into capillary plate 87, with seal 88, shown as a washer, forming a gas tight seal between the $CO_2$ canister and the capillary plate. In some embodiments the canister and capillary plate are metal and the seal is a metal washer. Because the device is small compared to larger pressure vessels, the amount of force necessary to "crush" the seal (i.e., the metal washer) and make contact between the metal surfaces can easily be generated. When the canister is screwed into the capillary plate, contact 90 of the canister and contact 91 of the capillary plate blank come into contact with the metal washer such that there is metal-on-metal contact, and the metal washer creates a gas-tight seal around the two contact points. The threads on the canister and capillary plate also enhance the seal. Additionally, a seal created by metal-on-metal contact between the two contact points and the threads doesn't rely on an elastomeric member such as an O-ring (through which $CO_2$ can permeate) to seal off the passage between two metal members, and thus the metal-on-metal contact between points 90 and 91 with seal 88 around the contact creates a much better gas-tight seal than simply using an O-ring to create the seal. Additional exemplary driver components that can be incorporated into any of the systems herein can be found described in U.S. application Ser. No. 11/231,482, which is incorporated by reference herein.

Driver 80 also includes solenoid housing 82, core 84, coil 85, and spring/seal assembly 86. The center of spring/seal assembly 86 is actuated to the left in the figure in response to a magnetic field generated by current being passed through coil 85. The leftward movement of the center of the spring/seal assembly opens the outlet to the valve orifice, allowing the release of the $CO_2$. Stopping the electrical current through the coil causes the magnetic field to cease, thus causing the spring assembly and rubber seal to return to a position which closes off the orifice. This stops the release of $CO_2$.

Figure 7A:
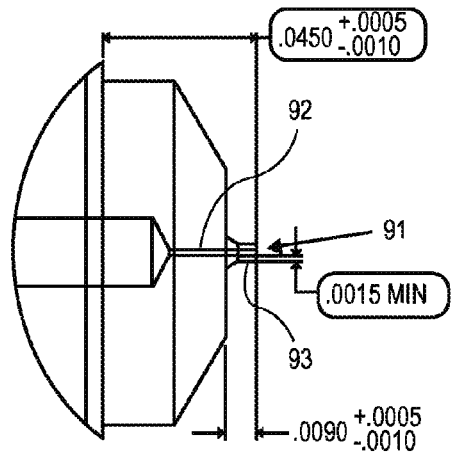
FIGS. 7A-7E show features of an exemplary valve orifice.
Figure 7B:
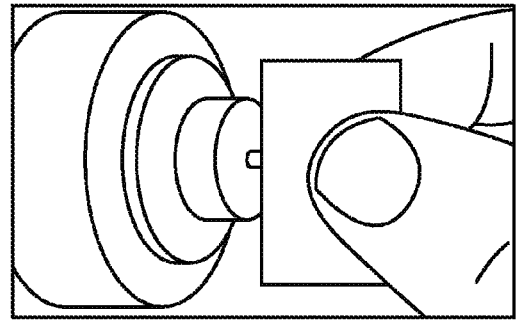
Figure 7C:
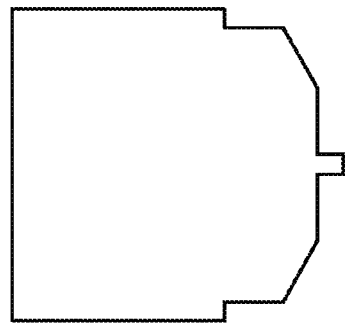
Figure 7D:
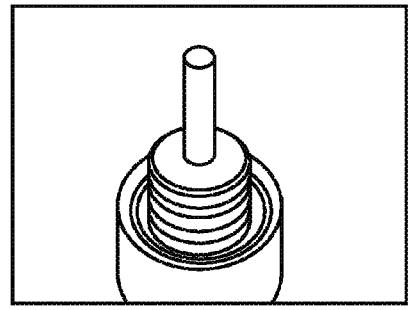
Figure 7E:
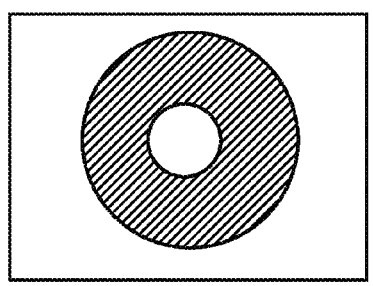

In the exemplary embodiment shown in FIG. 6, capillary plate 87 and the valve orifice are made from one piece, or are integral with one another. In some embodiments the capillary plate is stainless steel. FIGS. 7A-7E illustrate portions of the capillary plate including valve orifice 91, a lumen defined by the surface of channel 92, and outer surface of valve orifice 93. In some embodiments the valve orifice diameter (the inner diameter of lumen defined by channel 92) is about 0.001-0.005 inches, for example, about 0.002 inches. In some embodiments the outer diameter 93 is about 0.004-0.015 inches, for example, about 0.006 inches. The other dimensions shown in FIG. 7A are also in inches. The lumen of channel 92 can be formed by, e.g., micro-drilling. The small inner diameter of the valve orifice allows the orifice to act like a flow restrictor. The channel 92 also has a very small diameter and thus also acts as a flow restrictor and can vary or tune the volume dispensed per a given period of time. FIG. 7E shows an end view of the orifice in which the darkened region in the middle is the lumen defined by channel 92.

In some embodiments of assembling the solenoid shown in FIG. 6, an epoxy glue is injected into holes 92 in solenoid housing 82 to glue all of the solenoid components together at the same time.

Figure 8:
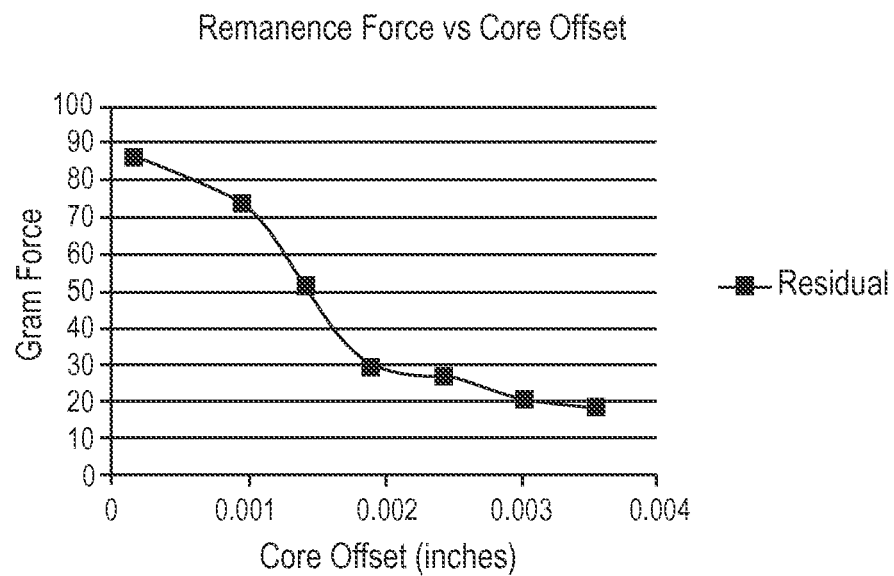
FIG. 8 illustrates remanence force vs. solenoid core offset.

In a solenoid valve, a magnetic remanence can occur in the magnetic material after the magnetic field is removed. This can cause the solenoid valve to stay open longer than desired. In the implants described herein, a valve which stays open longer than desired can result in too much $CO_2$ being released into the internal chamber which can reduce the accuracy of the remote controller's tracking of the estimated fill volume, described below. In some embodiments the core is offset (e.g., to the left in FIG. 6) by a certain amount, or a shim can be disposed between core 84 and the spring assembly to reduce the amount of magnetic remanence. FIG. 8 shows the residual remanence force vs. core offset (in inches), showing that the further the core is offset, the less the remanence force.

Figure 9:
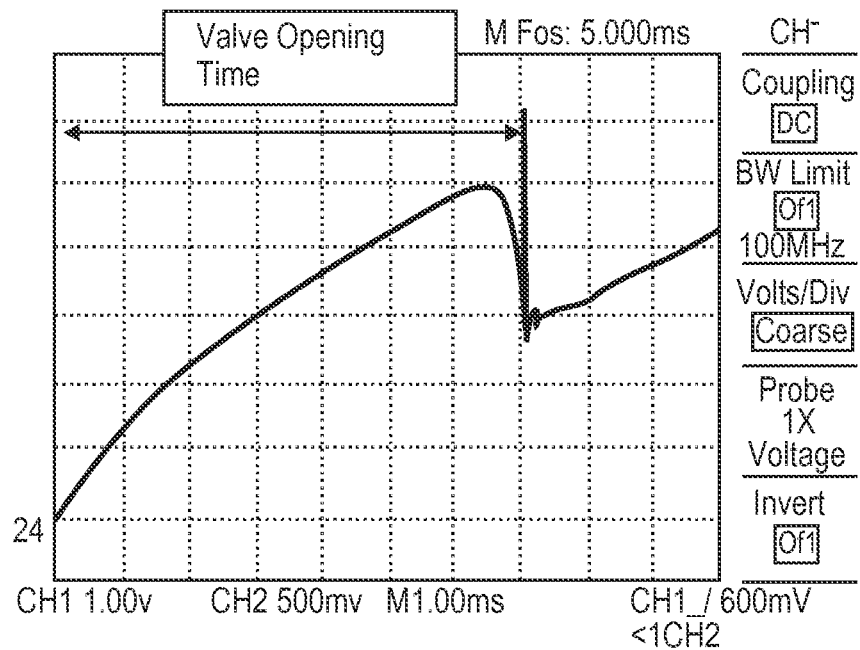
FIG. 9 illustrates an exemplary solenoid current measured over time, indicating the valve opening time.

The valve's performance can be tested by measuring the solenoid current (measured as voltage across a resistor) over time. The valve's open time can be determined from this measurement to meet internal specifications. FIG. 9 shows an exemplary solenoid current measured over time, which shows the "valve opening time."

The volume of gas that is released by a canister each time the actuation button on the remote control is actuated can be determined during testing by weighing the canister after each time the button is depressed. This volume determination is factored into the software as described below.

FIGS. 10A-10C illustrate an exemplary embodiment of a magnetic enhancement pad to prevent saturation of a central part of a spring. A spiral spring is shown which can be used in the spring/seal assembly 86 shown in FIG. 6. When current runs through solenoid coil 85, magnetic flux is generated in the inner disc 102 and inner disk can become magnetically saturated. The spring as shown includes outer annular element 100 and inner disc 102, which are connected by connecting portions 110 at hinge elements 104, 106 and 108. The spring also includes a second disc 120 attached to disc 102 by, example, spot welding. Second disc 120 helps to prevent the spring center from becoming magnetically saturated and it responds better to the magnetic field (i.e., it has more magnetic permeability). This allows more force to be applied to the central part of the spring to open the valve.

Figure 11:
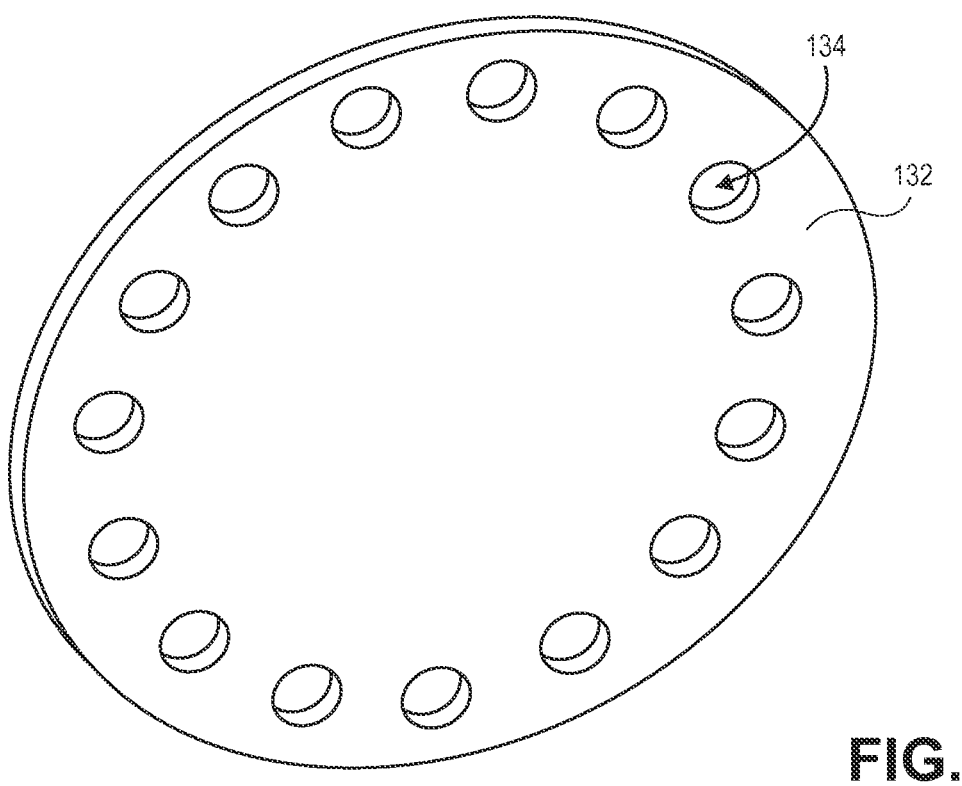
FIG. 11 illustrates an alternative embodiment of a magnetic enhancement pad.

FIG. 11 illustrates a magnetic enhancement pad 132 that can be used as an alternative to disc 120 shown in FIGS. 10A and 10B. Pad 132 is formed with a plurality of bores 134 therethrough generally around the peripheral portion of the pad. Creating the holes in the pad provides a pad with less mass than disc 120, which does not have any holes. In use, once the magnetic field ceases, the spring assembly accelerates the pad 132 (or disc 120) attached thereto toward the valve orifice, resulting in an impact (and therefore closing off the valve). A pad with less mass, such as pad 132, applies less of an impact force on the valve orifice when the spring assembly moves towards the closed configuration. Less force applied by the pad translates into less wear on the valve, which adds reliability, safety, and increases the life of the valve.

In use, the implantable portion is adapted to be positioned within the patient in a collapsed configuration in which the inner chamber is not in the expanded configuration. The collapsed configuration eases the insertion of the implantable portion into the patient. The implant can be positioned within the patient in any suitable location in which tissue is to be expanded. In some methods of use, the implantable portion is positioned within a patient following a mastectomy. In such embodiments the implant can be positioned in, for example, a sub-muscular, partially submuscular, or subcutaneous position in the region of the removed breast tissue.

After the implantable portion is positioned within the patient, the remote controller is actuated to release the fluid from the fluid reservoir, through the valve, and into the inner chamber. A "burp" is referred to herein as the event in which fluid is released from the reservoir. The periodic or continuous release of the fluid into the expandable inner chamber causes the inner chamber to expand over time, which causes the expansion of tissue proximate the implant. Once the tissue has been expanded to the desired degree of expansion, the implant can be removed from the patient and a permanent implant can replace the temporary implant.

The remote controller is adapted to control the amount of fluid that is released from the fluid reservoir over time. When the user actuates the actuator on the remote controller, the valve within the driver opens and releases the fluid, such as $CO_2$, from the reservoir into the expandable inner chamber.

The tissue expansion system comprises various electronic components to perform the functions described herein. The electronic components can be disposed in the remote controller, the implant, or some of the electronics can be disposed in the controller while some are disposed in the implant. In general, the tissue expansion system includes electronic components that allow the remote controller to wirelessly communicate with the implant and provide power thereto to control the release of fluid from the fluid reservoir. In some embodiments, such as those described above, the implant includes an antenna adapted to communicate with the driver. The antenna is adapted to be electromagnetically coupled with an antenna in the remote controller upon actuation of the remote controller such that actuation of the remote controller induces current to flow through the solenoid coil to open the valve, thereby releasing the fluid from the reservoir. In this manner the remote controller is adapted to provide power to the implantable implant via inductive coupling. In order to facilitate the transmission of temporary power to the driver, the antenna of the external device and the implantable devices must be in within a certain range of each other. Transmission of power between the remote controller and the implant can alternatively be carried out through a radiofrequency link or other types of wireless links.

In some embodiments the remote controller includes a power source, such as a rechargeable battery, to provide power to some or all of the system's electronic components. The implantable portion may also comprise a power source to provide power to electronic components within the implantable portion.

In some embodiments the electronic components may include one or more memory devices (e.g., RAM, Flash) to store information, such as information about the expansion of the expandable chamber.

The remote controller can also include one or more outputs for providing information to the patient as well as inputs for receiving instructions from the patient. The outputs can include audio outputs, visual outputs, and tactile outputs such as vibrations. The inputs can be actuators such as buttons, knobs, touch screens, microphones, etc.

The electronic components may optionally include circuitry and/or a microprocessor adapted to execute software, such as, for example without limitation, an algorithm that compares the total volume of gas that has been released from a gas source into the expandable chamber with a preset maximum fill volume. The software can additionally be programmed with limits on the dose amounts (including dose/burb, dose/time period) and the frequency with which doses may be administered. In some embodiments the processing component is disposed in the remote controller and includes any algorithms programmed with the limits on the dosages and with the limits on the frequency with which doses may be administered. In some embodiments, when the remote controller is actuated, the processing component is adapted to compare the number of times fluid has been released from the fluid source within a given period of time with a maximum number of times fluid is allowed to be released from the fluid source within the given period of time. If the number of times that fluid has been released within a given period of time is greater than or equal to a maximum number of times fluid is allowed to be released from the fluid source within the given period of time, the remote controller will not initiate the release of fluid from the fluid source (i.e., the valve will remain closed), and can be further adapted to provide an output to the user, such as an audible beep or the illumination of lights to indicate that an error has occurred. In some embodiments the remote controller is adapted to turn off. Exemplary limits that can be programmed into the processing component include a maximum of 1 dose (which is made up of one or more burps) about every hour to 1 dose about every 24 hours. In some embodiments the maximum dose is 1 dose about every hour, while in some embodiments the maximum dose is 1 dose about every three hours, but it can also be, for example, two doses about every 5 hours. For example, if the limit is one dose every hour, and the user actuates the actuator two times within 1 hour, the remote controller will not release fluid from the fluid source upon the second actuation. These quantities are merely exemplary and not intended to be limiting.

In some embodiments, when the remote controller is actuated, the processing component compares the volume of fluid that has been released from the fluid source within a given period of time with a maximum volume of fluid that is allowed to be released from the fluid source within the given period of time. If the volume of fluid that has been released within a given period of time is greater than or equal to a maximum volume of fluid that is allowed to be released from the fluid source within the given period of time, the remote controller will not initiate the release of fluid from the fluid source, and may provide an output to the user as set forth above. Exemplary limits that can be programmed into the processing component include a maximum volume limit from about 5 mL to about 100 mL every 24 hours. In some embodiments the daily allowable volume is from about 10 mL to about 50 mL. For example, in some embodiments the daily volume limit is about 30 mL in about every 24 hours. In use, a strict 24 hour limit can be burdensome on the patient's daily routine, so a limit that is generally 24 hours (e.g., 20-22 hours) can be programmed into the system instead. These are all considered to be about 24 hours. In some embodiments the processing component is programmed with a maximum 3 hour volume limit. For example, in some embodiments the system is programmed with a limit of about 10 mL for about every 3 hours.

The processing component can also be programmed with limits on the amount of fluid that is released during a single dose, or during a single burp. In some embodiments when the remote controller is actuated, a processing component is adapted to prevent more than a maximum volume of fluid from being released from the fluid source. For example, in some embodiments the system can be programmed to release about 1 mL to about 50 mL per dose, 1 mL to about 40 mL per dose, 1 mL to about 30 mL per dose, 1 mL to about 20 mL per dose. In some embodiments the system can be programmed to release about 5 mL to about 15 mL per dose. In some embodiments the system is programmed to release no more than about 10 mL per dose. If the system detects that more than 10 mL has been released during a single dose, the remote controller can be shut off, the valve can be automatically closed, or other actions can be taken to prevent additional fluid from being released. In some embodiment the dose is comprised of a plurality of burps. An integer number of burps can be used to approximate the desired dose, or a combination of full and partial burps may be used to provide a more finely tuned dose amount.

The processing component can also be programmed to estimate the total amount of fluid that has been released from the fluid source. Upon actuation of the remote controller, the processing component compares the total amount of fluid that has been released from the fluid source into the inner chamber with a maximum fill volume for the implantable component. This can prevent overexpansion of the implant beyond a pre-established limit. If the processing component estimates that that total amount of volume released from the gas source is above a maximum fill volume, the remote controller will prevent the release of gas upon further actuation of the remote controller, unless, for example, a periodic maintenance volume is required as described herein.

In some embodiments the implantable fluid is $CO_2$, and the $CO_2$ will leak out of the inner bag/outer shell assembly over time. While the inner bag can be adapted to provide for a $CO_2$ barrier, some $CO_2$ will diffuse through the layers of the inner bag over time. $CO_2$ can diffuse through the molecular structure of polymers, and is essentially impossible to completely contain within polymeric material. To determine the level of $CO_2$ permeability through an inner compartment, a known amount of $CO_2$ is released into an inner compartment, and the inner compartment is submersed in saline. $CO_2$ will diffuse through the inner compartment over time and into the saline. Periodic measurements of the volume of the inner compartment are made over time, which provides for an estimate of the rate of $CO_2$ permeation. In some embodiments the inner compartment is permeable between about 0 and 3 mL/day.

The processing component can be adapted to account for the permeation rate of the gas in some or all of its computations. For example, the processing component can factor the permeation rate into the total amount of gas that has been released from the gas source to automatically adjust the total of amount gas that is disposed within the implant at any given time. The processing component can therefore allow for a sufficient volume of gas, which is equal to that lost due to permeation, to be released into the expandable chamber to make-up for the gas that permeated out of the implant. In use, after the full expansion of the implant has occurred, a patient may have to wait for a period of time (e.g., a month) before surgery can be performed to replace the implant with a permanent implant. During this waiting period some $CO_2$ can diffuse from the implant. Under these circumstances it may be necessary to perform periodic maintenance doses to release additional $CO_2$ from the reservoir into the internal chamber to compensate for the $CO_2$ that has diffused through the inner bag. This can ensure the tissue expansion remains at the level achieved after full expansion.

Figure 12:
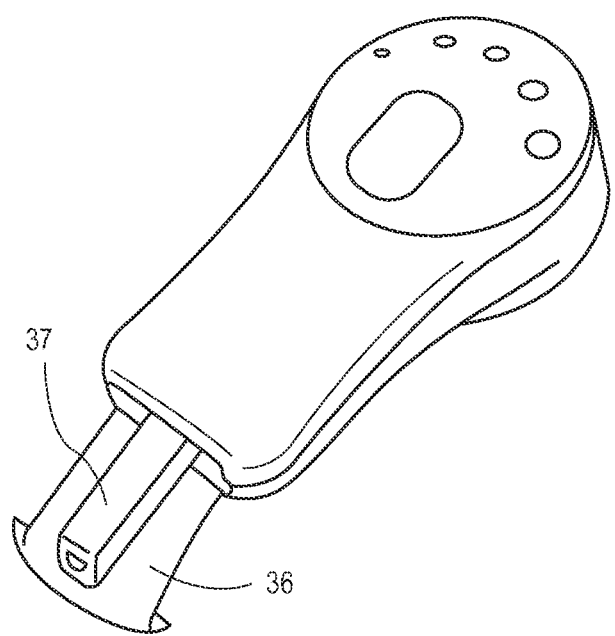
FIG. 12 shows an exemplary remote controller with a master key positioned therein.

The system can include a re-programming key to allow a physician to modify, or reprogram (permanently or temporarily) any of the programmed parameters using the re-programming key, a programming station, and/or an application on a separate electronic device, such as a computer or smart phone. The limits can be overridden by a physician with the use of the physician master key ("PMK"), an example of which is shown in FIG. 12. In FIG. 12, the remote control includes door 36, which can be opened to allow PMK 37 to be inserted to allow the physician to modify the existing system parameters.

In some embodiments the remote control, or the implantable portion, or both, include a memory component (either permanent of removable) which can store information relating to the use of the system, such as without limitation, date/time, error conditions, bad cyclic redundancy check ("CRC"), doses delivered, battery voltage, status (on/off), number of burps for a given dose, successful burps delivered, estimated volume of total gas in implant, estimate volume of gas remaining in the gas source, etc. The stored data can be extracted from the remote controller by a variety of known means, such as by incorporating a USB port into the remote controller, wirelessly downloading the information at a remote computer workstation, or transferring the information to a removable storage device such as a flash drive.

The following steps are exemplary method steps that can be carried out in one or more methods of using any of the tissue expanders disclosed herein. Not all of the method steps necessarily need to be performed when using a tissue expander. The order of any of the steps can also be modified in actual use.

Prior to initial use, the implant and the remote controller are bonded to one another, which prevents the remote controller from communicating with any other implant. The bonding step is typically performed by medical personnel before the implant is implanted, but can occur after the implantation as well, and can also be performed by the patient. In some embodiments the implant is one of four sizes and one of eight channels, which results in 32 configurations. In some embodiments the bonding can be performed only after a bonding key is inserted into the remote controller. Once the bonding key is inserted and an implant is bonded to the remote control, the remote control is bonded to that model and channel. The memory component, which can be disposed in the remote controller, reads and stores the following information from the bonding key: implant model number, implant channel number, implant Volume Fill limit (cc), canister dose calibration including dispense rate (cc/burp), implant permeation rate (cc/day), and starting implant volume estimate (cc) (normally set to 0). The parameters stored in the remote controller from the bonding step can be used in the limits calculations described above.

In an alternative embodiment, each implant includes a unique serial number chip. Before system use, a remote controller can be bonded once to a unique implant using this unique serial number chip. Following this bonding sequence, the remote controller will only recognize and dose an expander with that unique serial number. Alternatively, all bonding data could be stored in the implant and no key is used. The implant may have internal memory where it registers that it has been bonded to so that it will not accept a bond to another controller.

After storing the implant data from the bonding key or other initial data transfer, the total number of successful burps is set to zero, and the running total of estimated gas released will be set to the starting implant volume estimate. After storing the implant data, the remote controller erases this information from the bonding key to prevent it being downloaded by another remote control. A bonding key that has had its implant data erased can, however, function as a master key in any dose remote control with which it is used. After storing the implant data, the remote control enters into a detect mode.

Any of the following features can be programmed into one or more electronic components to occur during, e.g., the detect mode. Before entering detect mode, the remote controller updates the total implant volume based on the permeation rate of the implant. Upon entering detect mode, the remote controller will compare the total implant volume with the volume fill limit. If the total implant volume is equal to or greater than the volume fill limit, the remote controller will provide an output, such as an audio sound, or an illumination of the light indicators, and the remote control will turn off. Other types of error indication can be incorporated into the system. Upon entering detect mode, the remote control will compare the volume of gas released within roughly the last 24 hours with the 24 hour limit. If the volume released is equal to or greater than the 24 hour limit, error alert(s) will occur, and the remote control will turn off. Upon entering detect mode, the remote control compares the time since last successful dose to the minimum time between doses. If the time since the last dose is less than the minimum time between doses, an error alert will occur and/or the remote control will turn off. In detect mode if the remote control does not detect an implant, none of the indicator lights are illuminated. In detect mode, if an implant is detected the remote control shall read its model and channel number or serial number. In detect mode, if the remote control detects an implant that matches its bonded model and channel number, with an unacceptable coupling level, it will emit a sound indicative of the distance from the acceptable coupling region, and light a proportional number of the indicator LEDs of a given color. In detect mode, if the remote control detects an implant that matches its bonded model and channel number, with an acceptable coupling level, it will play an acceptable coupling sound indicative of the distance from the maximum achievable coupling, and light four or five (proportional with the % of maximum possible coupling) indicator LED's of a certain color. If, while in detect mode, with the implant sufficiently charged and the power coupling of a sufficient level to be able to complete the dose, the actuator in the remote controller is actuated to deliver a dose. Sufficient charging and power coupling is indicated by the remote controller when 4 or 5 LED's of a given color are lit The remote controller can be programmed to perform any of the following functions while in dose mode. Upon entering dose mode the remote controller shall command the implant to release the desired dose which is the lesser of the prescribed dose amount, the roughly 24-hour dose limit minus the dose given in the last 24 hours, the implant fill limit minus the total estimated gas released, and the prescribed dose amount minus the dose given in the last release (minimum time between doses). A burp is generated by holding the implant valve open for about 0.250 seconds+/−0.002 seconds, although this time is not intended to be limiting. The dose shall be applied by commanding an integer number of burps. The remote controller shall wait a minimum of 0.250 seconds between burps. The number of burps applied in a given dose shall be calculated such that neither the roughly 24 hour dose limit nor the implant fill limit will be exceeded; the prescribed dose should not be exceeded by more than about 25%. The memory component can store a history of the time and estimated successful total volume delivered after each dose. The memory component maintains a running total of the estimated total implant volume. The memory component maintains a running total of the number of successful burps administered. The processing component can calculate the amount of gas released per burp based on the running total of the number of successful burps administered and the canister dose calibration provided at the time of bonding. Between burps, if the remote controller detects that the implant is not making adequate progress charging the implant, it shall indicate a failed dose and return to detect mode. Between burps, if charging takes more than a specified amount of time (e.g., 3 seconds), the remote controller indicates a failed dose by providing an appropriate output to the patient (e.g., a visual or audio output), and then returns to detect mode. Before each burp the remote controller shall verify that the implant model and channel number match the remote controller's bonded implant and model number. If they do not match the remote controller will provide an error output and turn off.

As discussed above, a master key can be used to override the programmed limits of the system to allow a physician to control the release of fluid outside of the set limits. When a master key is positioned in the remote controller or is in communication with the remote controller, the 24 hour maximum limit can be over ridden. When a master key is in the remote control, the minimum time between doses shall be set to 0. When a master key is in the remote control, all doses shall be the prescribed dose. When the prescribed dose is not made up of an integer number of burps, a remote controller with a master key can round up the applied burps per dose. After the master key is removed from the remote controller, the previously programmed limits shall again be enforced.

The system optionally includes a limit key, which is a key that can be inserted into the remote controller and used to replace the original limits with those stored on the limit key. When a limit key is detected, the remote controller shall replace its stored limits with those from the limit key. After the new limits have been stored, the controller shall re-read the limits from the key and compare them to the stored limits. After successfully programming the limits, if the key is removed the device enters detect mode.

The system can optionally include an override key which is adapted to be inserted into the remote controller. When an override key is in the remote controller, the 24 hour maximum limit shall be overridden; the minimum time between doses shall be set to 0; the maximum fill limit shall be overridden; and all doses shall be the prescribed dose. When the prescribed dose is not made up of an integer number of burps, a remote controller with an override key can round up the applied burps per dose. When an override key is inserted, the remote controller shall write the contents of its log file to the override key. When writing the log file to an override key, the remote controller may overwrite previous log files. Log files on the override key shall contain a header including the date and time file was written, and model and channel number of the implant the controller is bonded to. After the override key is removed from the remote controller, previously programmed limits shall be enforced.

In some embodiments the memory component maintains a log file of specified system interactions. For each requested dose an entry is made in the log file comprising: date and time, number of burps calculated for that dose, number of successful burps in that dose, and implant volume estimate at the end of the dose. Each time the remote controller is turned on a log entry can be made comprising: date and time, implant volume, and battery voltage. Before the remote controller turns off the remote controller can make an entry in the log file including: date and time, number of bad CRC messages since power on, and the last error code. In the event of log file memory limitations, the newest records shall be retained and oldest records erased (first-in-first-out).

In some embodiments the memory component stores treatment and device functionality information. In some embodiments the information is stored in the implant and the remote control can therefore be universal—the remote control is not bonded to a specific implant and no patient-specific data is stored on the remote control.

Figure 14:
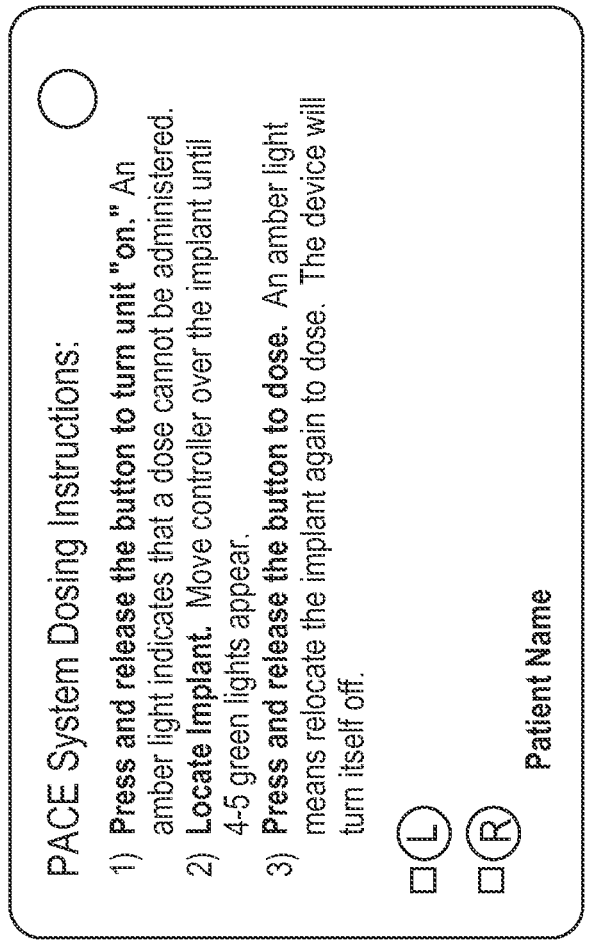

The disclosure above describes some exemplary methods of use in the context of the remote control functionality (e.g., bonding functionality, master key overriding, etc.). An exemplary quick reference guide for a physician is shown in FIG. 13. FIG. 14 illustrates an exemplary quick reference guide for a patient which provides dosing instructions. In addition to the patient dosing instructions, one example of the implantable device suggests that the patient should be advised not to travel by air during expansion, not to travel by ground transportation involving an ascent greater than about 1000 meters, and that if pain is increasing in severity over several hours, not to add more volume and to call the physician.

In some embodiments the physician will choose an implant from a kit of implants, or from a number of implant sizes which are available. The size of the implant can be based partially on patient parameters, such as the chest wall dimensions of the patient. In some embodiments the implants are 20% larger in volume than the corresponding permanent implant. Table 1 provides an exemplary list of 4 differently-sized implants and their respective properties, from which the physician can select one for implantation.

TABLE 1

Implants

| Surface | Shape/Profile | Size | Width (cm) | Height (cm) | Projection (cm) | Volume (cc) |
| --- | --- | --- | --- | --- | --- | --- |
| Textured | Anatomical | Small | 10.5 | 10.0 | 9.0 | 400 |
| Textured | Anatomical | Medium | 12.0 | 11.0 | 10.0 | 650 |
| Textured | Anatomical | Large | 13.0 | 12.0 | 11.0 | 850 |
| Textured | Anatomical | Full | 14.5 | 13.5 | 12.0 | 1100 |

The guiding aspect of dosing is dependent on patient comfort. If the patient is experiencing only minimal discomfort, the release of gas can generally be continued, according to the limits on the parameters programmed into the system. Allowing the patient to control the amount of tissue expansion based on the level of discomfort provides an exemplary advantage over other tissue expansion techniques because the expansion can occur more continuously than previous treatments, which may allow for lower pressures and less total expansion time.

Once the labeled volume of the implant has been achieved, the ability to add additional volume is significantly decreased to avoid over-pressurization of the implant. At this point, the processing component will generally only allow for a volume release equal to the slow permeation of gas from the gas reservoir.

In some embodiments the implantable portion includes one or more pressure relief valves that are configured to relieve a specific amount of gas from the expandable inner chamber to relieve pressure within the inner chamber. A potential use for the pressure relief valve is in altitude management. As the altitude of the patient in which the implant is implanted increases, the external pressure decreases and the gas inside the implant expands. In some embodiments the system includes a pressure sensor, which can be in the implantable portion or the remote controller (which should be maintained at the same altitude as the patient during travel). The pressure sensor monitors the pressure/altitude, and the memory component can log readings. If the pressure sensor is disposed within the remote controller, the remote controller can be adapted to monitor the pressure each time it is turned on, or to make periodic pressure readings while it is turned on. The remote controller can be adapted to control opening of the pressure relief valve in the implantable portion, either automatically or after prompting a user to actuate the remote controller. In some embodiments the pressure sensor is disposed within the implant, and if the implant has a power source it can automatically open the pressure relief valve, or the sensor could send a communication signal to the remote controller to alert the patient to actuate the remote controller, which would open the relief valve. The remote controller can be adapted to have a first actuator to release gas from the reservoir and a second actuator (such as a button) to control the opening of the relief valve.

The memory component in the system can also record the volume of gas that has been vented from the implant. The volume record would be used to calculate how much gas should be released from the canister to compensate for the vented gas after the patient has returned to a lower altitude. The remote control can also be adapted to provide an output to warn the patient if the venting is too frequent so that sufficient gas does not remain within the gas reservoir to compensate for the vented volume.

FIGS. 15A-H illustrate exemplary relief valve concepts that can be incorporated into any of the tissue expander systems disclosed herein. In some embodiments, the pressure is released from the inner chamber and the relief valve does not reseal. In others, the relief valve has the capability of resealing.

Figure 15A:
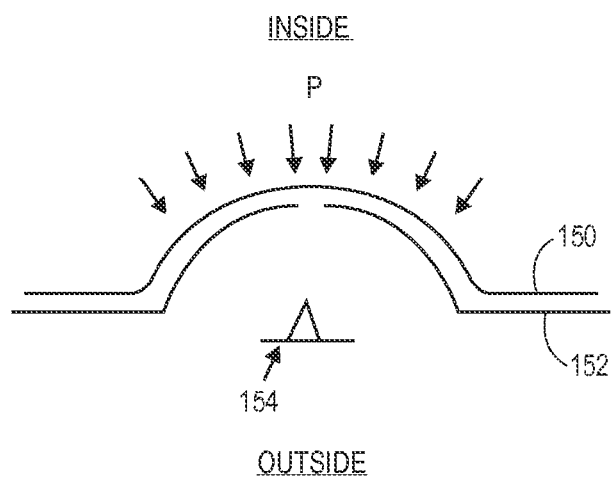
FIGS. 15A-15H illustrate exemplary relief valve concepts.

FIG. 15A illustrates a portion of an implant in which at least a portion of the barrier layer 150 of the inner bag is bonded to an inverted dome 152. When the pressure "P" inside the inner bag increases, it can cause dome 150 to invert, or pop out, causing the piercing element 154 to pierce a portion of barrier file 150, releasing gas out of the inner chamber. Piercing component 154 can be bonded to another part of the inner bag, or even to the outer shell.

Figure 15B:
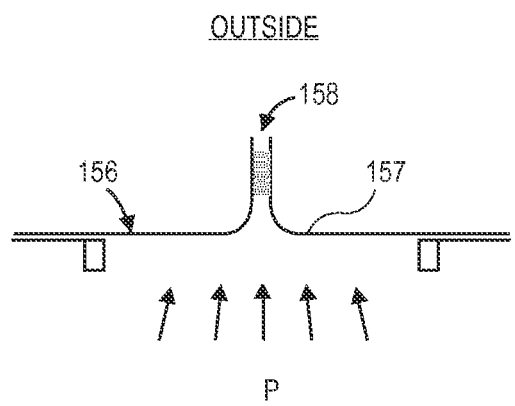

FIG. 15B illustrates a portion of an implant in which a first portion 156 of the barrier film and a second portion 157 of the barrier film are bonded together at location 158, such as by heat staking. As the pressure "P" inside the inner chamber increase, it causes the heat staked film to separate, releasing gas out of the inner chamber.

Figure 15C:
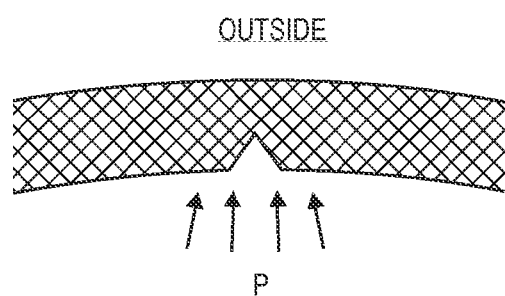

FIG. 15C illustrates a portion of an implant in which a piercing element 159 is formed or secured to a heat staked area. When the pressure "P" inside the inner bag increases enough, the piercing element will pierce through the inner bag and release gas from the inner chamber.

Figure 15D:
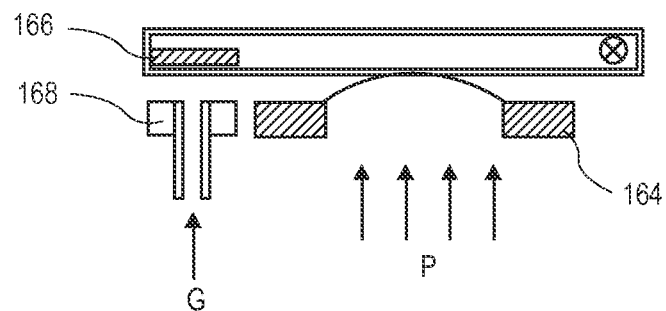

FIG. 15D illustrates a portion of an implant in which film 162 is secured to barrier layer 164. Lever arm 166 includes a magnetic material, as does magnetic ring 168. As the pressure "P" inside the inner chamber increase, film 162 bows as indicated, moving lever arm 166 away from magnetic ring 168. This allows gas to escape in the direction of arrow G shown.

Figure 15E:
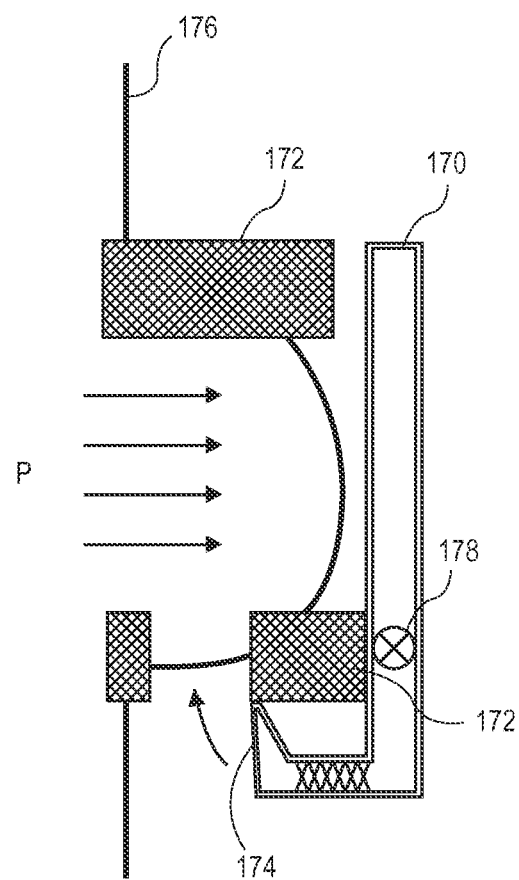

FIG. 15E illustrates a portion of an implant in which lever arm 170 rotates about point 178 as it is pushed by film disc 172, when the film disc is under pressure. After arm 170 rotates to a certain degree, the arm's piercing element 174 snaps into a second region of the film disc. This releases gas from the inner chamber.

Figure 15F:
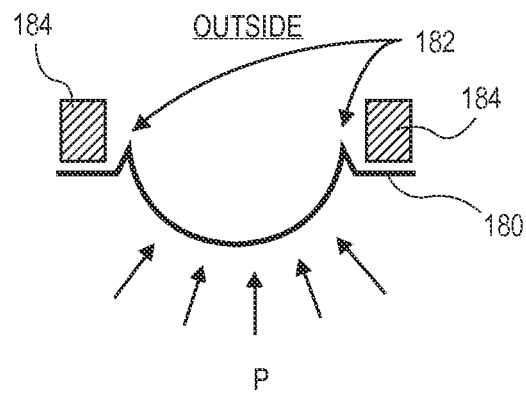

FIG. 15F illustrates a portion of an implant in which foil (or other suitable material) dome 180 is adapted to invert upon an increase in pressure "P." When it inverts, the regions 182 where the stress in concentrated will tear, allowing gas to escape from the inner chamber.

Figure 15H:
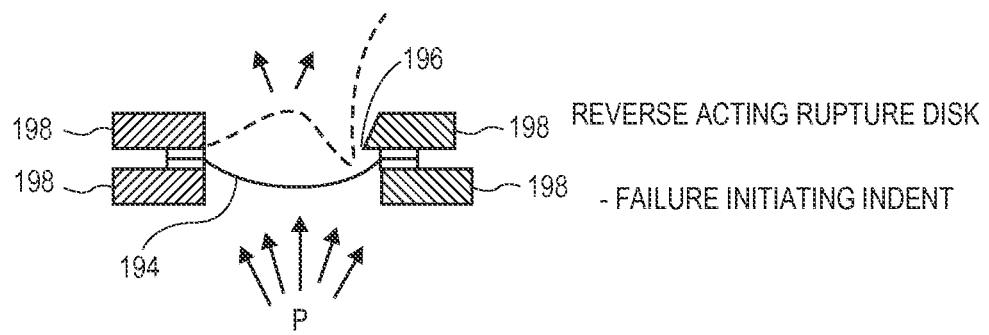
Figure 15G:
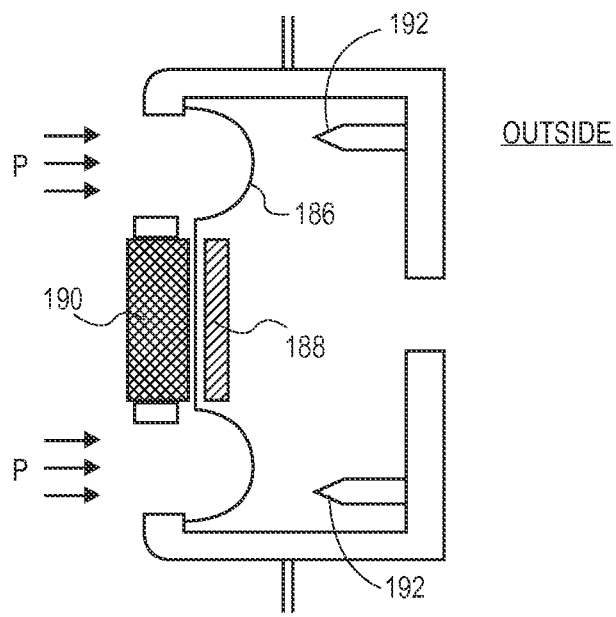

FIG. 15G illustrates a portion of an implant in which magnetic materials 190 and 188 bias the film inward. As the pressure "P" inside increases, film 186 bows outward as shown, wherein the plurality of piercing elements 192 pierce the film 186, allowing gas to escape.

FIG. 15H illustrates a portion of an implant in which film 194 is maintained between layers 198 of a rupture disc. The rupture disc includes a failure initiating indent 196, which is adapted to tear film 194 as pressure "P" increases and pushes film 194 into indent 196.

In some embodiments a valve includes a magnetic material and the valve is opened when a second magnetic material is moved in close proximity to the first magnetic material. This vents the gas and deflates the tissue expander prior to, for example, radiation therapy. The valve can be re-sealable. When the magnet is removed, the valve closes and the inner bag can be re-filled with additional gas from the reservoir in the driver. This approach can also be used to vent gas if the patient has to travel to altitude and is experiencing pain or discomfort from the expansion of the gas within her implant. Alternatively, the inner bag can be filled with a liquid such as saline using any of the methods described below. In some embodiments the relieve valve is electronically activated an actuator housed in the remote controller.

Figure 16:
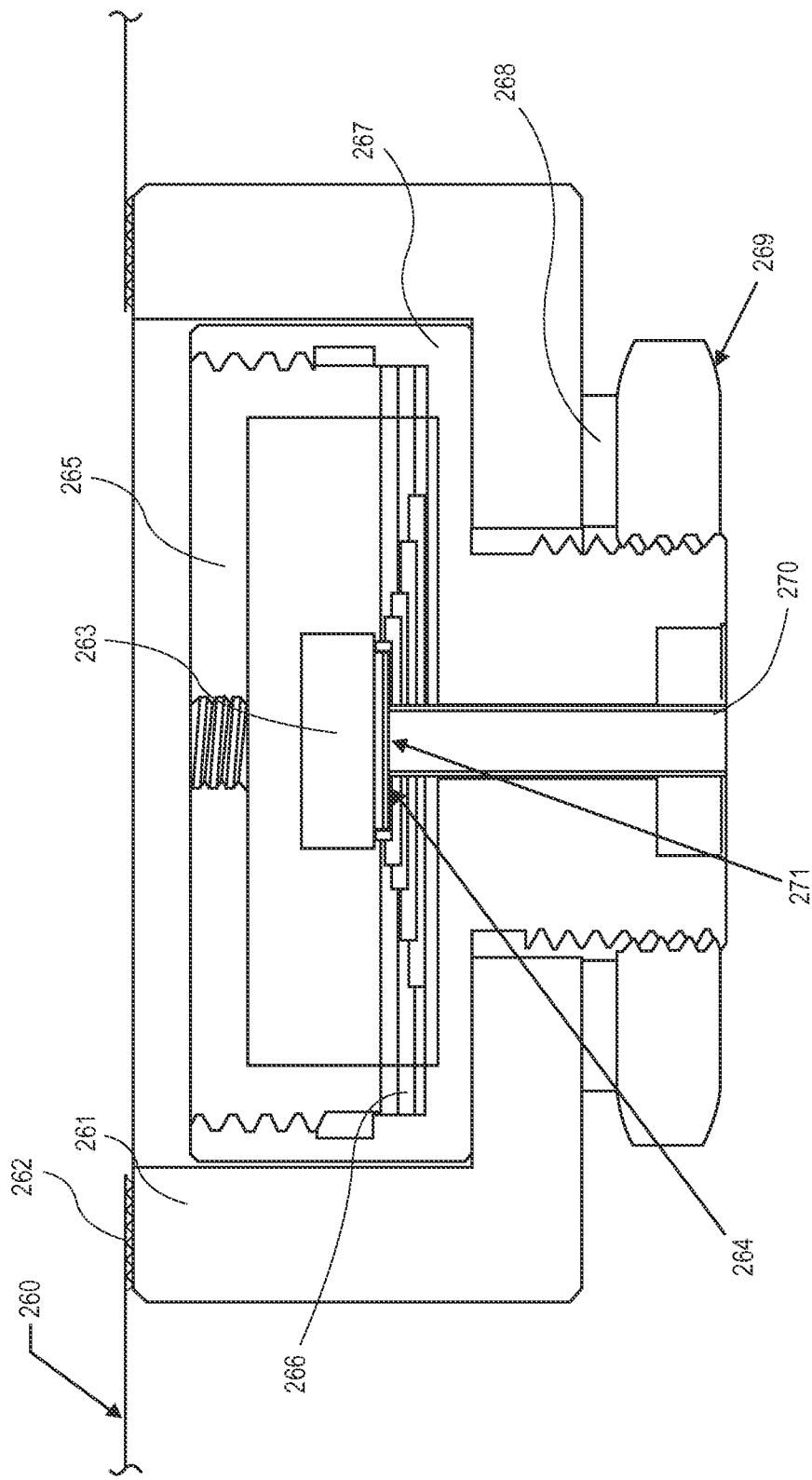

FIGS. 16 and 17 illustrate an exemplary embodiment of a pressure relief valve with a resealing capability that can be incorporated into any of the tissue expanders disclosed herein. As shown in FIG. 16 the pressure relief valve includes flow control tube 270 fixed and sealed to an outer valve housing 267 using adhesive. Inner valve housing 265 is threaded into outer valve housing 267 and retains spring/seal assembly 264 and shims 266 that determine the desired amount of valve opening. Valve seat 271 on the end of flow tube 270 is smoothed to insure a leak-free seal with the elastomer portion of spring/seal assembly 264 when the valve is closed. Valve magnet 263 is mounted and fixed to spring/seal assembly 264 using adhesive. The valve housings are retained within retention ring 261 that provides the ability to heat seal 262 the valve to inner bag 260. Retention nut 269 compresses seal washer 268 and the portion of retention ring 261 between outer valve housing 267 and seal washer 268, thus, providing a seal between the valve housing and the retention ring.

As shown in FIG. 17, the valve is opened by bringing control magnet 275 into close proximity to valve magnet 263. This causes the valve magnet that is attached to the spring/seal assembly to move in the direction of the arrow. The movement of the spring/seal assembly opens the valve, allowing gas to flow out of the inner chamber through the lumen of flow control tube 270 and past valve seat 271 as indicated by the arrows.

Some embodiments of the tissue expander are adapted to have fluid removed after the fluid has been released from the reservoir into the inner chamber inside the patient. An example of this is the use of the pressure release valves described above to release gas from the inner chamber when the pressure becomes too great. There are additional potential situations in which it is desirable to release, or remove, fluid from the implant. For example, some current radiation therapy protocols for women who have undergone a mastectomy involve deflating the tissue expander after it has been expanded within the patient, therapeutically radiating the tissue, and then re-expanding the device again after completion of radiation therapy.

Some of the embodiments that provide for the release of gas from the implant provide for one or more of the following features: 1) deflating a gas-filled expander by venting the gas, in some embodiments inside and in others outside of the body; 2) re-inflating the expander with a fluid such as saline or gas. Any suitable components of any of the embodiments described below may be incorporated into a tissue expansion system to provide a pressure relief valve.

If re-inflating the expander with saline, the outer shell (which can be comprised of silicone material) is adapted to retain saline like traditional saline expanders. In some embodiments described above, however, the outer shell is perforated to allow air between the inner bag and the outer shell to escape for ease of insertion into the patient during implantation. In embodiments with a sealed outer shell to retain the saline, there would therefore be a requirement for an alternate method of venting air from between the inner bag and the outer shell during implantation.

These embodiments provide the physician the option of implanting a device that could be deflated and subsequently re-inflated. It also may provide the physician the option of forfeiting such a capability by removing the components which provide this functionality from the primary expander, such as in cases where the likelihood of post-operative deflation/re-inflation is very low (prophylactic mastectomy, small tumors far from the chest wall, etc.). Thus, a portion of the device could be removed if desired.

Figure 18A:
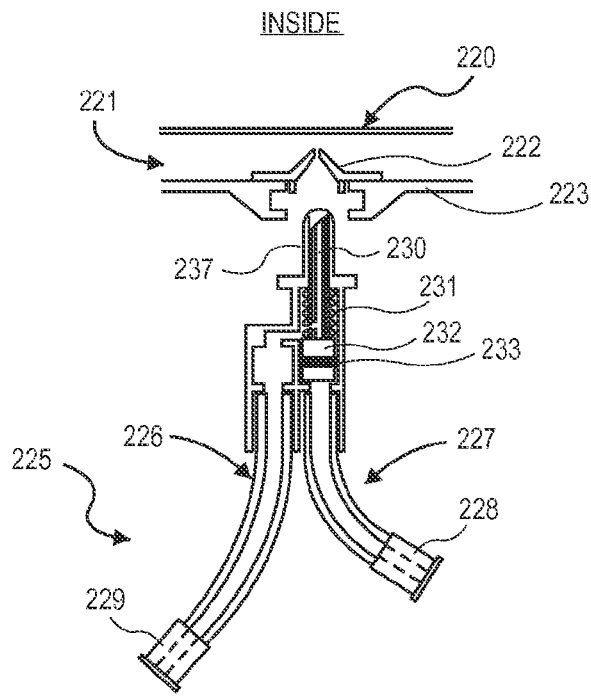
FIGS. 18A-C illustrate an exemplary mechanism for releasing a fluid from one or more regions of a tissue expander and for filling a region of the tissue expander with a fluid.
Figure 18B:
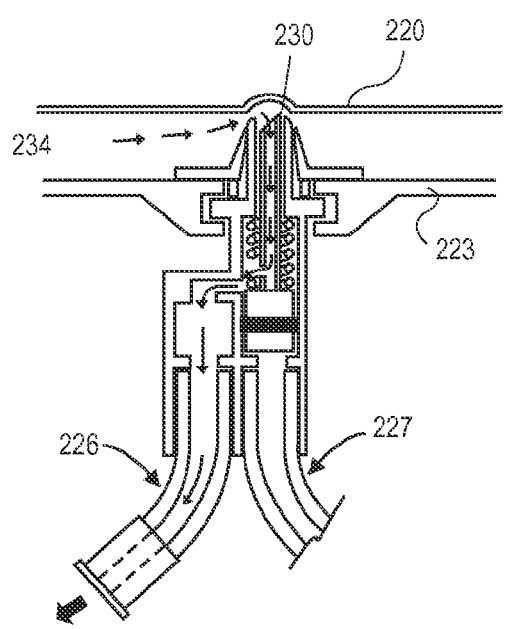
Figure 18C:
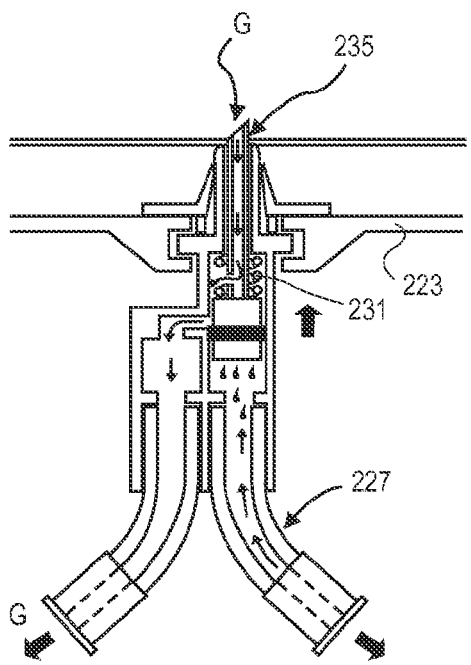

FIGS. 18A-C show a portion of an exemplary implant that includes docking port 224 formed integrally with outer shell 223. One-way remote valve 222 is secured to outer shell 223. Docking port 224 and valve 222 are adapted to receive device 225 that is adapted to release fluid from or fill fluid into the implant. Device 225 has fill/drain tubing 226 and needle injector tubing 227 each terminating with a luer fitting 229 and 228, respectively. Device 225 also includes fenestrating cannula 230, compression spring 231, piston 232, and seal 233.

In FIG. 18A, one-way valve 222 is in a closed configuration, and cannula or needle 230 is retracted inside device 225. Until central cannula 237 is docked with port 224, the one-way valve remains closed and air is trapped between the inner bag and the outer shell. The inner bag is intact and provides the gas barrier within the tissue expander.

Prior to implantation of the implantable portion into the patient, any air that has diffused through the outer shell (shown in FIGS. 18A and 18B as made out of a silicone material) into the space between the inner bag and the outer shell may be removed. If it is not removed, the implant will feel partially inflated and will make insertion to the target region more difficult. FIG. 18B shows device 225 docked with port 224, and cannula 237 has forced valve 222 into an open configuration, creating a passage for air to flow from the space between the inner bag and the outer shell. Air 234 trapped between inner bag 220 and outer shell 223 can be vented from the space between inner bag 220 and outer shell 223 using a syringe attached to fill/drain tube 226, as indicated by the directions of the arrows shown. In FIG. 18B, inner bag 220 remains intact and continues to provide the gas barrier within the implant. Fenestrating cannula or needle 230 remains withdrawn inside central cannula 237.

FIG. 18C illustrates a use of device 225 and valve 222 to remove gas from the inner chamber of the implant. As mentioned above, some patients require radiation therapy after a tissue expander has been expanded. If the patient requires radiation therapy and the protocol recommends deflation of the implant prior to radiation therapy, gas in the implant may need to be removed. Needle injector tube 227 is filled with pressurized liquid (either through a fitting exposed through the skin or via a remote fill valve punctured with a transcutaneous needle). The pressure from this injected fluid displaces piston 232 upward, compresses spring 231, and deploys fenestrating cannula 230 from central cannula 237, causing cannula 230 to puncture inner bag 220 at location 235. Gas "G" is then vented through cannula 230 and out of tubing 226, as illustrated by the direction of arrows. In some embodiments the gas is vented outside the body. The action shown in FIG. 18C irreversibly punctures inner bag 220, converting it to a fluid controlled expander similar to saline expanders currently on the market. After the radiation therapy or other therapy is complete, port 242 can be located, punctured with a needle and the inner chamber can be filled to the desired volume with a fluid such as saline.

Figure 19:
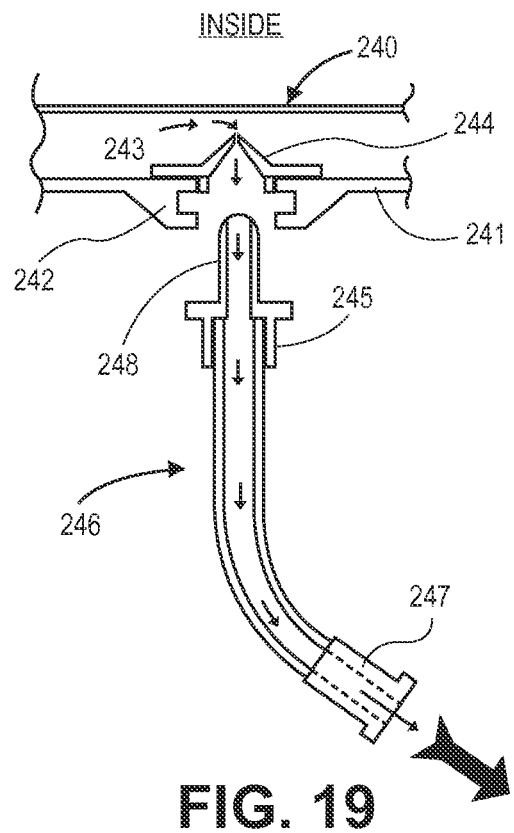
FIG. 19 illustrates an exemplary mechanism to remove fluid from a region of a tissue expander.

FIG. 19 illustrates a portion of an alternative embodiment of an implant with a dedicated docking port 242 at a separate location on outer shell 241. This design separates the feature for venting air from the space between the inner bag and outer shell from the implant deflation/inflation feature. Tubing 246 is coupled to central docking cannula 248 (similar to the central cannula in FIGS. 18A-C) and luer fitting 247. This device does not have a fenestrating, spring-loaded cannula with the second piece of tubing as shown in the variation in FIGS. 18A-C. The device in FIG. 19 can be used to aspirate air from between inner bag 240 and outer shell 241 prior to implantation. Prior to implantation, cannula 248 and tubing 246 are removed from docking port 242.

One advantage of the approach in the embodiment in FIG. 19 is that it eliminates the implantation of the remote fill port. A temporary tubing is used to remove the air from the space between the inner bag and the outer shell (as shown in FIG. 19) and then is detached from the implant prior to implanting the implant within the patient. The outer shell is designed to hold saline at pressures encountered during tissue expansion.

Figure 20:
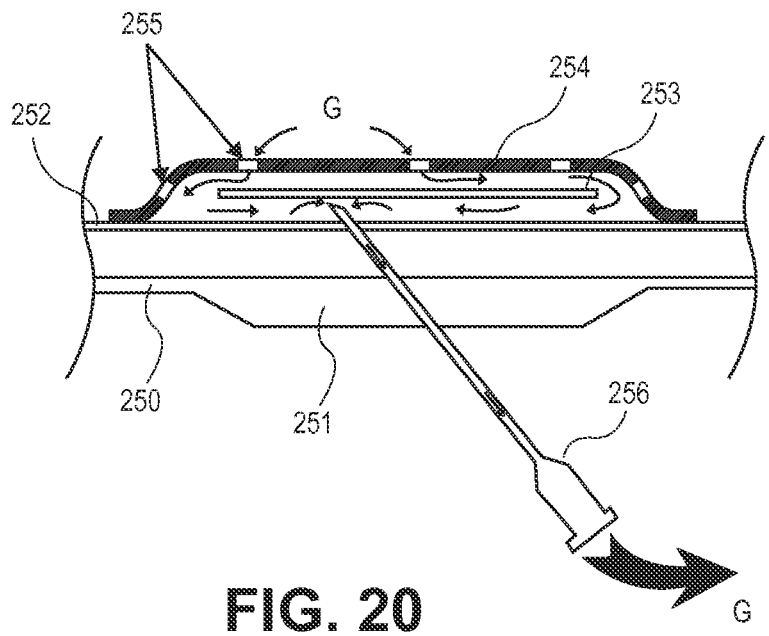
FIG. 20 illustrates an exemplary mechanism to remove fluid from a region of a tissue expander.

The implant shown in FIG. 19 can additionally include an intrinsic injection port such as the injection port shown in FIG. 20 to remove fluid such as gas from the inner chamber. Deflation of the implant prior to radiation therapy is accomplished by targeting and inserting a needle 256 (e.g., 25G) into intrinsic port 251 which can be disposed in the anterior, superior portion of outer shell 250 for ease of locating. Needle 256 passes through 251 intrinsic port and penetrates inner bag 252. Once the inner bag is breached by the needle, gas in the inner chamber can be vented from the implant into the ambient atmosphere.

Antenna 253 can be constructed of a tough material such as a polyimide material that resists needle penetration. In some embodiments, the antenna is heat staked continuously with a gas impermeable membrane 254 to the inside of inner bag 252. As shown in FIG. 20, this type of assembly can be modified to allow gas "G" to escape. In particular, vent holes 255 can be formed around the antenna which allows gas from within the implant to pass therethrough and out through needle 236.

Once radiation therapy is complete, needle 256 can again be inserted into intrinsic port 251 and saline can be injected into the inner chamber to achieve the desired volume. During re-inflation, the needle need not penetrate the inner bag. Saline only needs to fill the outer shell to the desired volume.

In embodiments that include an intrinsic port, the intrinsic port can include any or all of the following features: the needle port is in the superior anterior portion of the implant and reseals after repeated insertions of a needle; it is robustly attached to the elastic material of the inner bag so that pressurized saline will not leak out of the inner bag; and a needle stop to prevent the needle from fenestrating the posterior panel of the implant and causing a leak. It is noted that the intrinsic port concepts shown can be implemented with or without an integral needle stop. Additionally, if the intrinsic port does not include an integral needle stop, alternate methods of protecting the posterior panel of the inner bag can be employed (not shown in the figures, but it can be accomplished, for example, by reinforcing the posterior panel with impenetrable component-like polyimide film).

In tissue expander implants that include antennas, the injection point can be located in the middle of the antenna and its location can be established using the antenna-locating ability that exists in the remote controller. Alternatively, a separate external device specifically tasked to locate the antenna and port can be developed with an integral needle guide. This locating needle guide can use the electromagnetic coupling with the antenna to guide the needle into the desired zone for needle puncture.

The exemplary embodiments described in FIGS. 21-24 illustrate alternative intrinsic needle ports, and illustrate how an intrinsic needle port can be attached to an anatomically-shaped inner bag of a tissue expander to maintain a leak-proof, saline-filled bladder and to preserve the low permeation performance of the inner bag. Configurations are shown both with and without a component acting as a needle stop.

Figure 21A:
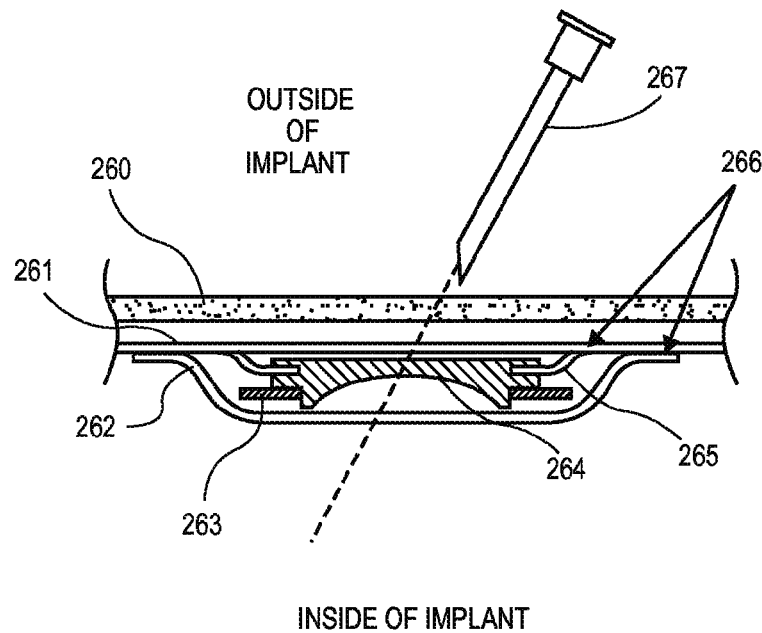
FIGS. 21A-24B illustrate exemplary embodiments of an implant with an intrinsic needle port.
Figure 21B:
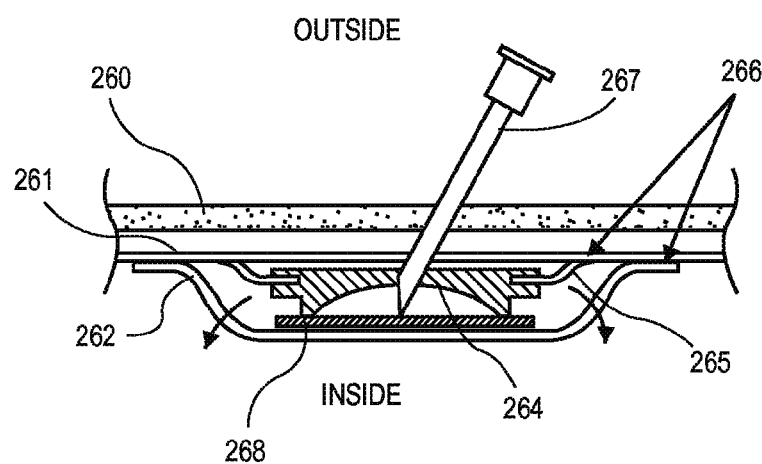

FIGS. 21A and 21B illustrate an exemplary embodiment of an implant with an intrinsic needle port. The intrinsic port as shown includes a silicone re-sealable injection port 264 molded around port flange 265 (see FIG. 21A). Since port flange 265 is insert molded within the silicone port 264, a leak-proof connection between the two components retains saline within the implant. Port flange 265 is shaped like a washer with a raised rib to improve the durability of the connection between it and injection port 264. Port flange 265 can be made from a thermoplastic material such as polyethylene to facilitate attachment to inner bag 261 with either a heat staking or ultrasonic welding, for example. Heat staking provides a leak-proof attachment. Antenna 263 is shown outboard of injection port 264 and is made from flexible circuit material such as polyimide encapsulated copper traces. It is positioned and fixed coaxially with injection port 264 using a thin film of thermoplastic, such as polyethylene, using heat staking or ultrasonic welding methods. Antenna 263 and injection port 264 are retained by antenna patch 262, which is also heat staked to inner bag 261.

Prior to the use of the needle and in embodiments in which gas is used as the initial filling medium, injection port 264 is mounted so that inner bag 261 remains completely intact until needle puncture. This ensures that inner bag 261 does not excessively lose gas due to permeation through injection port 264 or its attachment point.

When injection or aspiration is required, needle 267 is inserted through outer shell 260, through inner bag 261, and into port 264, and through antenna patch 262 and into the inner compartment. When the needle is removed, the liquid contents of the implant can pass through antenna patch 262 through the hole created by needle 267 and pool below injection port 264. However, liquid cannot pass through silicone re-sealable injection port 264 or around injection port 264 to escape through the needle hole in inner bag 261 located above injection port 264. Inner bag 261 therefore remains inflated with saline with no leaks.

FIG. 21B shows the embodiment from FIG. 21A but includes needle stop 268. The needle stop is incorporated in this assembly by placing a component below injection port 264. The needle stop can be a plastic or metal disk such as polyimide. In the embodiment shown, the needle stop is combined with the antenna (combined as 268) to make the overall port more compact. To position and fix needle stop 268 below the port, a thin film 262 of thermoplastic material such as polyethylene can be heat staked to the inner bag.

The embodiments in FIGS. 22-24 have similar architectures to the embodiment shown in FIGS. 21A and 21B. An exemplary difference is the specific method of attaching the silicone injection port to the inner bag film in a robust, leak-proof manner.

Figure 22A:
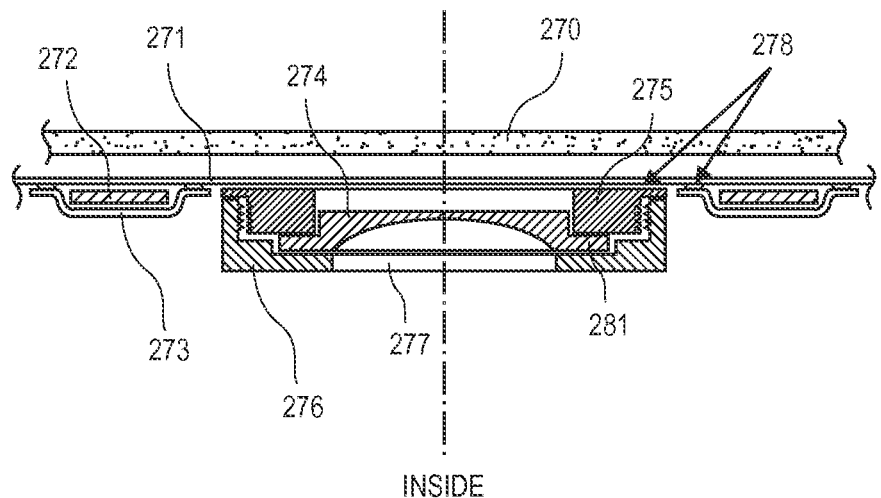
Figure 22B:
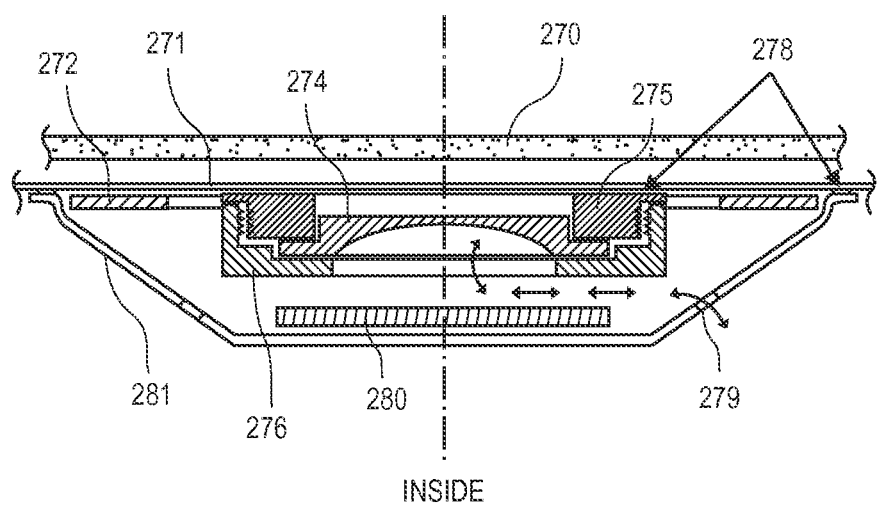

FIGS. 22A and 22B illustrates a method of attaching silicone injection port 274 to inner bag film 271 in a robust, leak-proof manner. Plastic ring 275 with a threaded portion and a thru hole is heat staked to the inside of inner bag 271 at region 278. Injection port 274 is mounted within ring 275 and is retained by plastic nut 276. Flange portion 281 of injection port 274 is crushed as plastic nut 276 is tightened, thus creating the seal. Antenna 272 is retained in place by patch antenna 273. A needle can be used in the same way as illustrated in FIG. 21A, passing through opening 277 in nut 276.

FIG. 22B shows the addition of needle stop 280 retained in position by needle stop patch 281 in a similar manner to the embodiment in FIGS. 20A and 20B. Alternatively (not shown), plastic nut 276 can be constructed without a through hole through the middle of the nut providing a thickness of material to stop the needle. Additional vent holes can be added to the plastic nut in a region away from where the needle might contact such as through holes that exit radially from the nut. Vent holes 279 are formed in patch 281 to allow gas to pass in and out of the patch 281 into the port area. A needle can be used in the same way as illustrated above.

Figure 23A:
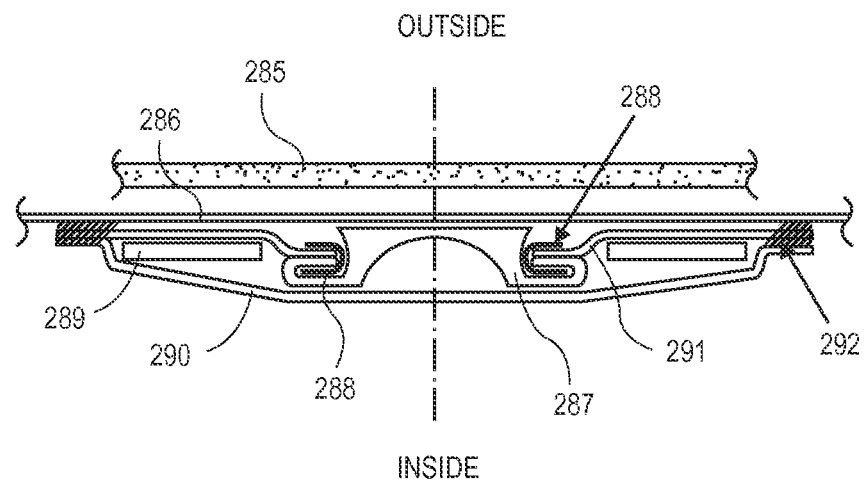
Figure 23B:
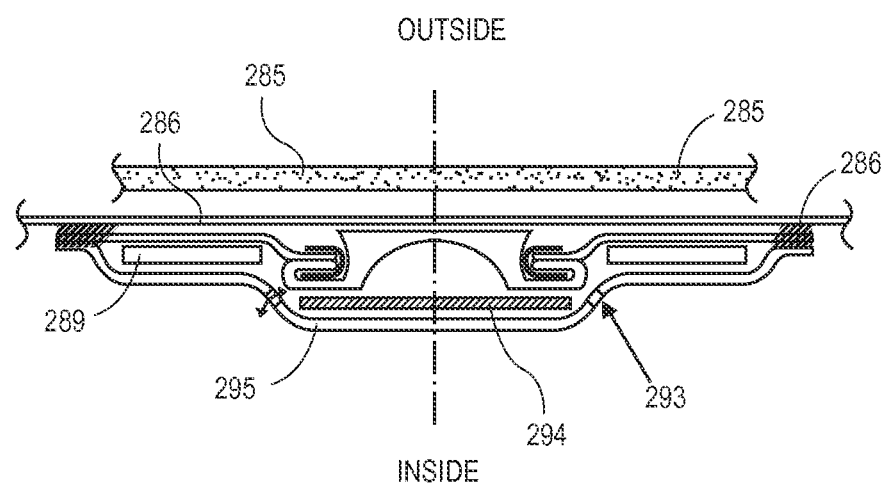

FIGS. 23A and 23B illustrate a method of attaching silicone injection port 287 to inner bag film 286 in a robust, leak-proof manner. Crimping component 288 is shaped like a grommet and can be fabricated from metal. When deformed with the proper tool, the crimp can pinch and capture both a flange on injection port 287 and the inside region of washer 291 made of thin plastic film. Crimp 288 forms a waterproof seal between these components. Subsequently during assembly, plastic washer 291 can be heat staked to the inside of inner bag 286 at location 292. Antenna 289 is positioned outboard of crimp 288 and retained by antenna patch 290, which is heat staked to the inside of inner bag 286. A needle can be used to penetrate into the implant though shell 285 as set forth above.

FIG. 23B shows the addition of needle stop 294 retained in position by needle stop patch 295 in a similar manner to the embodiments in FIGS. 21 and 22. Similar components to those in FIG. 23A have the same reference number.

Figure 24A:
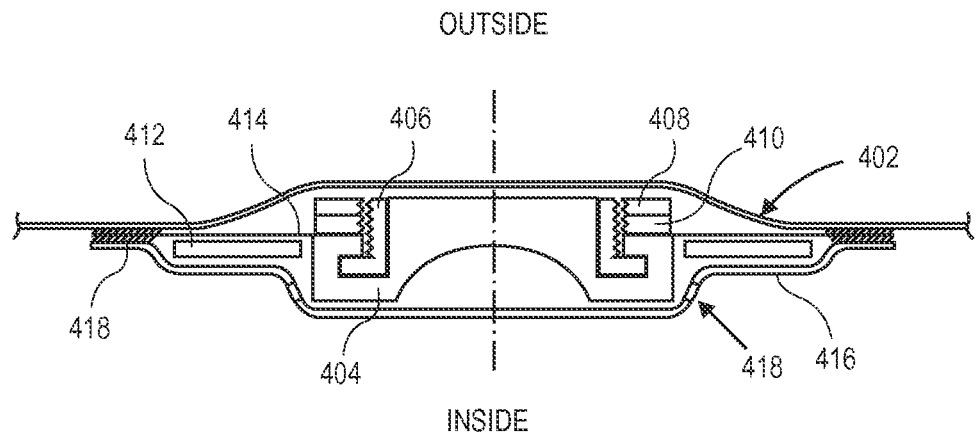
Figure 24B:
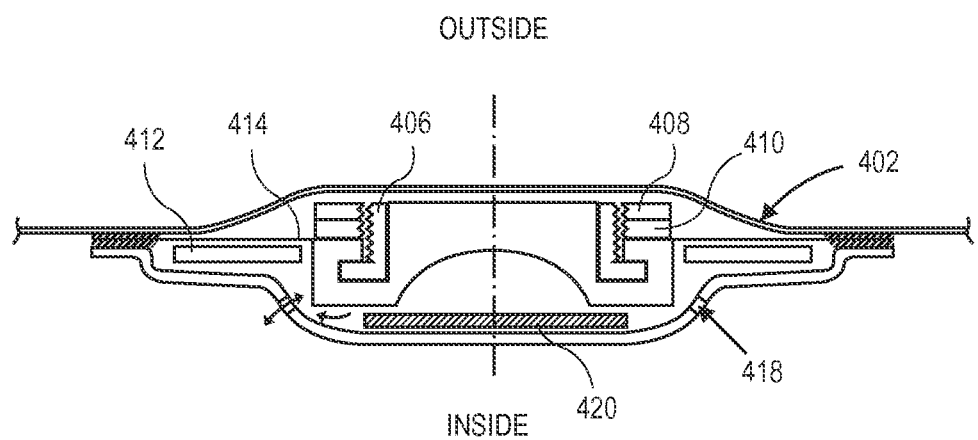

FIGS. 24A and 24B illustrates a method of attaching silicone injection port 404 to inner bag film 402 in a robust, leak-proof manner. Insert ring 406 and nut 408 are used to clamp three thin members together: the flange from injection port 404, thin film 414 shaped like a washer, and silicone washer 410. As shown in FIG. 24A, this clamping action forms a waterproof seal between these components. Subsequently during assembly, plastic washer 414 can be heat staked to the inside of inner bag 402 at region 418. Antenna 412 is positioned outboard of injection port 404 and retained by antenna patch 416, which is heat staked to the inside of inner bag 402. Vent holes 418 are formed in patch 416 to allow fluid to pass therethrough. A needle can be advanced through the port as described herein.

FIG. 24B shows the addition of needle stop 420 retained in position by needle stop patch in a similar manner to the embodiments shown in FIGS. 21-23. Other components are listed with the same reference number as in FIG. 24A.

While some of the embodiments described above are initially expanded with a gas, it may be recommended that some patients not be implanted with a device that is expanded with gas. For example, some patients may live in mountainous regions or may be required to travel by air or at higher elevations for their work—both activities could cause discomfort or pain if using a gas medium that will expand in the decreasing atmospheric pressure encountered at higher elevations. A physician may elect to use conventional saline-filled technology for a patient with these travel needs. In some embodiments described herein the tissue expanders include an anatomically-shaped inner bag. In-vivo, this anatomical shape provides subcutaneous volume in the desired location (e.g., the lower pole for breast implantation) where additional skin is needed. Saline-filled elastomeric tissue expanders generally do not accomplish this. For breast reconstruction, the elastomeric (silicone) tissue expander often takes the shape of a round balloon expanding tissue undesirably in the upper pole. Occasionally, the liquid-filled elastomeric balloon will expand laterally (under an arm) or superiorly (toward the clavicle). Traditional saline-filled tissue expanders can thus be improved by incorporating an anatomically-shaped component, such as the anatomically-shaped inner bags described herein.

Additionally, as described above, patients may also be identified early in their clinical treatment for breast cancer as needing radiation therapy. If several deflation and re-inflation cycles are indicated, a physician may elect for a more conventional saline-based expansion technology. Additionally, gas-inflating tissue expanders described above include a driver within the implant. The driver amounts to a mass of metal. Although saline expanders also contain metal, radiation oncologists may prefer not to plan their radiation dosing scheme with the new metallic components of the systems described herein until they are more familiar with it. Thus, anatomically-shaped, saline-filled tissue expanders could be an alternate solution for patients undergoing planned radiation therapy. In some embodiments a traditional saline-filled breast implant is enhanced with a component with an anatomical shape to ensure that additional skin is created where it is needed.

Additionally, some breast reconstruction patients do not have sufficient skin in the post-mastectomy region to cover a gas expanded tissue expander. The driver of the gas expander may add more bulk and projection to the tissue expander compared to a conventional saline-based tissue expander. A small percentage of breast reconstruction patients, whether undergoing immediate or delayed reconstruction, may benefit from a very low profile tissue expander. Anatomically-shaped, saline-filled tissue expanders with an intrinsic port could be very low profile solution for these patients. The intrinsic ports described herein can therefore be incorporated into traditional saline-filled expanders to provide for an expander with a desired anatomic shape, one that is comprised of relatively little metal to avoid radiation scattering during radiation therapy, and/or can be implanted with a very low profile.

Generally, the inner chamber of the implant should be sterilized in the event that a procedure must be performed on the patient that involves puncturing the inner chamber while it is inside the patient. Sterilizing plastics, which are included in the implants disclosed herein, with electron beam sterilization ("E-beam") or gamma sterilization can, however, cause the materials to become brittle and/or lose some of their properties. The electronic components of the implant can similarly be damaged from E-beam and gamma sterilization.

In some embodiments the inner chamber of the implant is sterilized with a gas such as ethylene oxide ("EtO"). The inner chamber, however, cannot simply be exposed to EtO because the gas cannot pass from outside the inner bag to the inside of the inner bag. During the manufacture of the implant, an inlet channel is provided from the inside of the inner bag to the outside of the inner bag, with a filter disposed over the outlet of the channel. The inner bag with the filter and channel assembly is then placed in the EtO chamber. The EtO passes through the filter, into the channel, and into the inner bag of the implant, sterilizing the inner bag. The filter is designed to keep any bacteria from entering the channel, but allows the gas to pass through it. A vacuum is then applied to the inner bag, removing the air from the inner bag, and the channel is heat-sealed shut, leaving the inner bag sterilized. The inner bag is then secured to the inside of the outer silicone shell. Next, the outer shell with the sterilized inner bag therein is placed in the EtO chamber, which sterilizes the outside of the inner bag and the silicone outer shell, as well as the rest of the packaging. The implant can therefore undergo a two-stage gas sterilization process without risking damage to the materials or the electronics.

If the implant includes a pressure relief valve with the capability to reseal, the pressure relief valve could be shipped in an open position to the sterilization facility. The inner bag could be held open for gas sterilization on the inside of the inner bag. There could also be a valve designed specifically for sterilization incorporated into the inner bag (either mechanical grenade pin or electrically activated by fixture or the remote control). In some embodiments the implant can be packaged with the valve open, followed by EtO sterilization. A vacuum is then applied to the inner bag, followed by closing the bag valve for final shipment. In some embodiments, the internal portion of the driver is sterilized separately from the rest of the inner bag using Tyvek™ to cover the vent holes in the solenoid to maintain the sterility of the inner volume and driver parts.

Figure 25A:
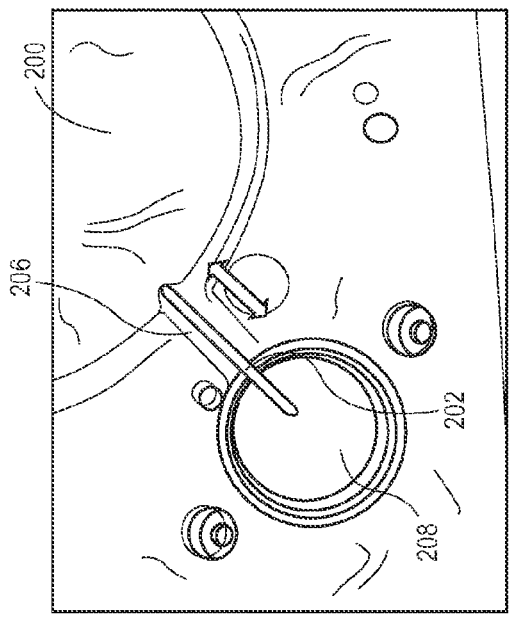
FIGS. 25A-D illustrate an exemplary method of sterilizing a tissue expander.
Figure 25B:
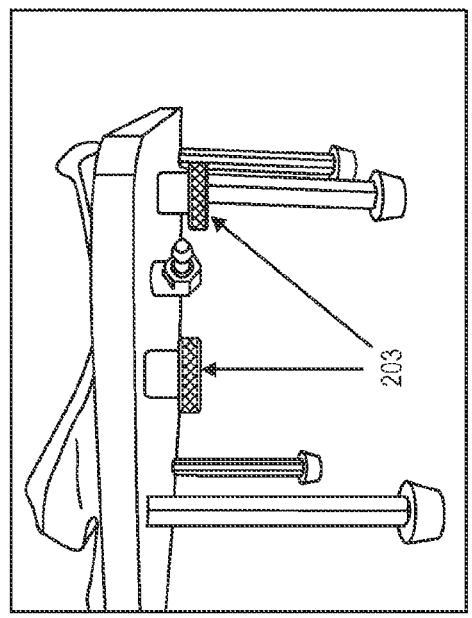
Figure 25C:
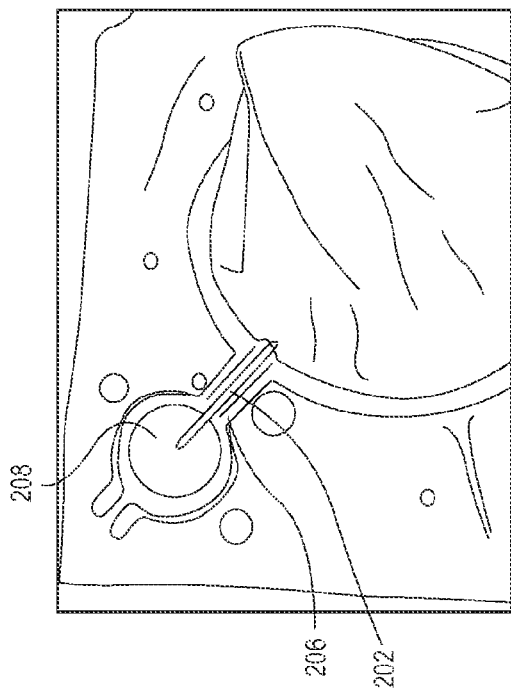
Figure 25D:
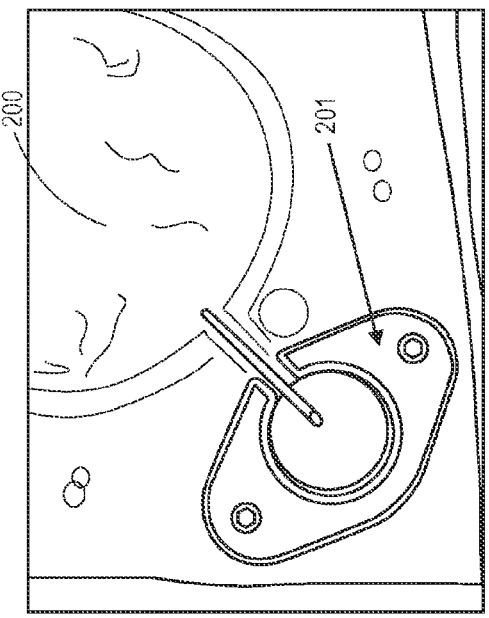

FIGS. 25A-D illustrate an exemplary method of creating a filter and tunnel system to sterilize the inside of inner bag 200 with EtO. FIG. 25A shows filter 208 in communication with inlet tunnel 206, in which pin 202 is disposed to keep the tunnel from collapsing during the vacuum stages of the EtO sterilization. FIGS. 25C and 25D illustrate the steps of positioning port clamp 201 and hand tightening thumb nuts 203, respectively, which provide access to draw vacuum on the inner chamber.

In some embodiments there is a final inspection of the packaged, sterilized product. The final inspection allows confirmation of both valve function and a leak check of the implant inner bag. The valve function can be verified by recording and analysis of the sound produced during solenoid valve opening when the valve is actuated by the remote control, i.e., "burped." In some embodiments, the sound can be detected and recorded using a contact microphone and then be subsequently analyzed using computer software to confirm that the valve opened and also determine the amount of time that the valve opened. The leak check of the final sterilized product is accomplished by using the remote control to actuate the valve and release a small amount of gas, i.e., burp the implant, while the implant remains in its package. The implant is then pressurized to squeeze gas out of any potential leak path and monitored with a sniffer specific to the gas used. The presence of excess gas indicates a leak.

In addition to any of the benefits described above, any of the tissue expansion systems described herein can provide one or more of the following advantages to the patient over previous tissue expansion systems (some of which may be described above): less discomfort; no needles are required; faster—complete reconstruction sooner; more rapid return to normal activity; fewer office visits; and ease of use. Advantages for the physician include no needles or office preparation time; reduced expansion time; earlier completion of reconstruction; ease of use; greater patient satisfaction; and less chance of complications than with injection-filling.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the invention.

What is claimed is:

1. A tissue expansion system, comprising:
    an implantable tissue expander comprising an inflatable chamber completely surrounding a compressed gas reservoir, wherein the inflatable chamber is a non-elastic chamber with a pre-formed shape and is adapted to assume the preformed shape when the inflatable chamber is inflated with a gas from the compressed gas reservoir; and
    an external controller adapted to wirelessly communicate with the implantable tissue expander to control the release of the gas from the compressed gas reservoir into the inflatable chamber to inflate the inflatable chamber towards the performed shape.

2. The system of claim 1 wherein the gas is irreversibly released from the compressed gas reservoir into the inflatable chamber.

3. The system of claim 2 wherein the implantable tissue expander further comprises a valve that is adapted to regulate the irreversible release of the gas from the compressed gas reservoir into the inflatable chamber.

4. The system of claim 1 wherein the implantable tissue expander further comprises a communication component adapted to wirelessly communicate with the external controller.

5. The system of claim 1 wherein the implantable tissue expander further comprises a pressure relief valve adapted to release gas from the inflatable chamber.

6. The system of claim 1 wherein the pre-formed shape is a breast shape with a lower pole extension.

7. The system of claim 1 wherein the inflatable chamber comprises a posterior backing and an anterior element secured to the posterior backing to define the inflatable chamber, wherein the anterior element is a non-elastic material and has the pre-formed shape.

8. The system of claim 1 wherein the compressed gas reservoir is secured to a posterior backing.

9. The system of claim 8 wherein the compressed gas reservoir is not rigidly secured to the posterior backing.

10. The system of claim 9 wherein the implantable tissue expander further comprises a housing for the compressed gas reservoir, wherein the housing is attached directly to the posterior backing and the compressed gas reservoir is not attached directly to the posterior backing, and wherein the compressed gas reservoir is disposed within the housing such that it is not rigidly secured to the posterior backing.

11. The system of claim 1 wherein the implantable tissue expander further comprises an external shell disposed around the inflatable chamber.

12. The system of claim 1 wherein the external controller is adapted to be actuated to control the release of gas from the compressed gas reservoir into the inflatable chamber to inflate the inflatable chamber, the system further comprising a processing component adapted to prevent more than a maximum volume of gas from being released from the compressed gas reservoir within a given period of time.

* * * * *